(12) United States Patent
Kurokawa et al.

(10) Patent No.: US 11,551,788 B2
(45) Date of Patent: Jan. 10, 2023

(54) INFORMATION PROCESSING SYSTEM, INFORMATION PROCESSING METHOD, AND PROGRAM

(71) Applicant: Inter-University Research institute Corporation Research Organization of information and Systems, Tokyo (JP)

(72) Inventors: Ken Kurokawa, Mishima (JP); Koichi Higashi, Mishima (JP); Hiroshi Mori, Mishima (JP)

(73) Assignee: Inter-University Research Institute Corporation Research Organization of Information and Systems, Tokyo (JP)

(*) Notice: Subject to any disclaimer, the term of this patent is extended or adjusted under 35 U.S.C. 154(b) by 837 days.

(21) Appl. No.: 16/480,539

(22) PCT Filed: Jan. 19, 2018

(86) PCT No.: PCT/JP2018/001594
§ 371 (c)(1),
(2) Date: Jul. 24, 2019

(87) PCT Pub. No.: WO2018/139361
PCT Pub. Date: Aug. 2, 2018

(65) Prior Publication Data
US 2019/0377744 A1 Dec. 12, 2019

(30) Foreign Application Priority Data
Jan. 26, 2017 (JP) .............................. JP2017-012340

(51) Int. Cl.
*G16B 40/20* (2019.01)
*G16B 40/00* (2019.01)
(Continued)

(52) U.S. Cl.
CPC ............... *G16B 40/20* (2019.02); *C12Q 1/00* (2013.01); *G16B 20/00* (2019.02); *G16B 30/00* (2019.02); *G16B 40/00* (2019.02); *G16B 45/00* (2019.02)

(58) Field of Classification Search
CPC ........ G16B 20/00; G16B 30/00; G16B 40/00; G16B 40/20; G16B 45/00; C12Q 1/00
See application file for complete search history.

(56) References Cited

U.S. PATENT DOCUMENTS 10,870,877 B2 * 12/2020 Embree .................. A23K 50/10

FOREIGN PATENT DOCUMENTS

| JP | 2007518972 | 7/2007 |
|---|---|---|
| JP | 2012080790 | 4/2012 |
| WO | WO 2014/046646 | 3/2014 |

OTHER PUBLICATIONS

Yan et al., "MetaTopics: an integration tool to analyze microbial community profile by topic model", The Author(s) BMC Genomics 2017, 18 (Suppl 1):962, pp. 1-5 (Year: 2017).*
Knights et al., "Bayesian community-wide culture-independent microbial source tracking." Nature methods 8.9 (2011), pp. 761-763.
Blei et al., "Modeling annotated data." Proceedings of the 26th Annual International ACM SIGIR Conference on Research and Development in Information Retrieval. ACM, 2003.
(Continued)

*Primary Examiner* — Ping Y Hsieh
*Assistant Examiner* — Jose M Torres
(74) *Attorney, Agent, or Firm* — Dority & Manning, P.A.

(57) ABSTRACT

An information processing system includes: a sample data acquisition unit that acquires, for each sample, sample data in which a first cluster and a second cluster are associated with each other, the first cluster including a plurality of sets of a biological element detected from the sample and a
(Continued)

biological element quantity indicating a quantity of the biological element, the second cluster including a plurality of sets of a morpheme regarding text describing an environment in which the sample is present and an appearance frequency of the morpheme; and a generation unit that analyzes a plurality of pieces of the sample data with the biological element quantity and the appearance frequency as parameters and generates information indicating a relationship between the environment and the first cluster.

9 Claims, 15 Drawing Sheets

(51) Int. Cl.
*G16B 30/00* (2019.01)
*G16B 20/00* (2019.01)
*G16B 45/00* (2019.01)
*C12Q 1/00* (2006.01)

(56) References Cited

OTHER PUBLICATIONS

Van der Maaten et al., "Visualizing data using t-SNE." Journal of Machine Learning Research 9. Nov. 2008, pp. 2579-2605.
Van der Maaten, Laurens, "Learning a parametric embedding by preserving local structure." RBM 500 (2009).
Henschel, et al., "Comprehensive meta-analysis of ontology annotated 16S rRNA profiles identifies beta diversity clusters of environmental bacterial communities." PLoS Comput. Biol. 11. 10 (2015): e1004468.
Arumugam, et al., "Enterotypes of the human gut microbiome." Nature 473. 7346 (2011), pp. 174-180.
PCT International Search Report dated Jan. 31, 2018, PCT Application No. PCT/JP2018/001594, 2 pages.

* cited by examiner

FIG. 5

| SAMPLE ID | CHARACTER STRING | APPEARANCE FREQUENCY |
|---|---|---|
| #sample1 | tonsil | 4 |
| | oral | 2 |
| | human | 5 |
| | ... | ... |
| #Sample | sludge | 2 |
| | wastewater | 1 |
| | city | 1 |
| | ... | ... |
| ... | ... | ... |

FIG. 6

| SAMPLE ID | NAME OF MICROBE | QUANTITY |
|---|---|---|
| #sample1 | Prevotella | 420 |
| | Escherichia | 10 |
| | Fusobacterium | 2 |
| | ... | ... |
| #Sample | Propinibacterium | 873 |
| | Staphylococcus | 302 |
| | Anaerococcus | 200 |
| | ... | ... |
| ... | ... | ... |

FIG. 15

SAMPLES OF TOP TEN OF RESULTS SEARCHED FOR
BY q=" Hot spring water"

| Sample ID | Score | Sample name |
|---|---|---|
| SRS465029 | 0.000449893 | hot springs metagenome |
| ERS124771 | 0.000413211 | marine metagenome |
| ERS124773 | 0.000405725 | marine metagenome |
| SRS465059 | 0.000399319 | hot springs metagenome |
| SRS005698 | 0.000398021 | marine metagenome |
| SRS005697 | 0.000378442 | marine metagenome |
| SRS465060 | 0.00037297 | hot springs metagenome |
| SRS428971 | 0.000340428 | hot springs metagenome |
| SRS374022 | 0.000335187 | hot springs metagenome |
| SRS465035 | 0.000326262 | hot springs metagenome |

FIG. 16

| SAMPLE ID | NAME OF GENE | QUANTITY |
|---|---|---|
| #sample1 | hsl0 | 20 |
| | tsaC | 15 |
| | butB | 107 |
| | ... | ... |
| #Sample | benB | 3 |
| | nuoB | 38 |
| | hisF | 320 |
| | ... | ... |
| ... | ... | ... |

FIG. 17

| SAMPLE ID | NAME OF MOLECULE | QUANTITY |
|---|---|---|
| #sample1 | GABA | 490 |
| | Acetate | 129 |
| | Acetyl CoA | 586 |
| | ... | ... |
| #Sample | Adenine | 98 |
| | Equol | 24 |
| | Genistein | 104 |
| | ... | ... |
| ... | ... | ... |

INFORMATION PROCESSING SYSTEM, INFORMATION PROCESSING METHOD, AND PROGRAM

TECHNICAL FIELD

The present invention relates to an information processing system, an information processing method, and a program.

Priority is claimed on Japanese Patent Application No. 2017-012340, filed Jan. 26, 2017, the content of which is incorporated herein by reference.

BACKGROUND ART

Recently, with a background of remarkable development in sequencing technology for deoxyribonucleic acid (DNA), metagenomic analysis has been actively performed to reveal microbial communities that inhabit natural environments by comprehensively sequencing DNA sequences included in samples of microbial communities acquired from various natural environments. A sample of a microbial community can be expressed using its structure as data while bacterial species constituting the microbial community are used as parameters.

Hereinafter, data indicating a microbial community structure will be referred to as microbial community structure data. A large number of species of bacteria constitute a microbial community. Therefore, sometimes, several hundreds of parameters are required to describe microbial community structure data.

PRIOR ART DOCUMENTS

Non-Patent Documents

[Non-Patent Document 1]
Dan Knights, et al, "Bayesian Community-wide Culture-independent Microbial Source Tracking", Nature Methods 8.9 (2011): 761-763
[Non-Patent Document 2]
David M. Blei and Michael I. Jordan, "Modeling Annotated Data", Proceedings of 26th Annual International ACM SIGIR Conference on Research and Development in Information Retrieval, ACM, 2003
[Non-Patent Document 3]
Laurens van der Maaten and Geoffrey Hinton, "Visualizing Data Using t-SNE", Journal of Machine Learning Research 9, November (2008): 2579-2605
[Non-Patent Document 4]
Laurens van der Maaten, "Learning a Parametric Embedding by Preserving Local Structure", RBM 500 (2009): 500
[Non-Patent Document 5]
Andreas Henschel, Muhammad Zohaib Anwar, and Vimitha Manohar, "Comprehensive Meta-analysis of Ontology Annotated 16S rRNA Profiles Identifies Beta Diversity Clusters of Environmental Bacterial Communities", PLoS ComputBiol 11.10 (2015): e1004468
[Non-Patent Document 6]
Manimozhiyan Arumugam, et al, "Enterotypes of the Human Gut Microbiome" nature 473.7346 (2011): 174-180.

SUMMARY OF THE INVENTION

Problem to Be Solved by the Invention

Incidentally, in order to identify microbial community structures which are unique to various natural environments, it is necessary to have pieces of data to which environmental labels indicating the environment where a sample was acquired are appropriately applied regarding a large number of pieces of microbial community structure data. However, there is a limitation on manual labeling in the current situation where the volume of data is increasing explosively.

In addition, in a current situation where microbial community structures originating in new environments which have not attracted attention until now are becoming clear one after another, it takes time and effort to take countermeasures with respect to this and to design a lexical system (ontology) of environmental labels defined with appropriate granularity.

Moreover, in a technique in which one environmental label is applied to one sample, it is not possible to appropriately evaluate a sample having intermediate properties of a plurality of environments. For example, Non-Patent Document 1 proposes that a certain microbial community structure be modeled in a state where microbial community structures of several environments are mixed. However, in the technique of Non-Patent Document 1, it is necessary for a user to set a reference microbial community structure of a mixture source. Therefore, it is difficult to appropriately design a reference microbial community structure which corresponds to every sample.

As described above, since it is difficult to perform interpretation or utilization of microbial communities, it is desired that interpretation or utilization of microbial communities be facilitated. In addition, recently, not only genomic information related to microbial communities but also a large amount of information (metatranscriptome and metabolome) regarding various biomolecule groups such as genetic products and metabolic products have been accumulated. Accordingly, it is desired that interpretation or utilization of biomolecule groups be facilitated.

An object of some aspects of the present invention is to provide an information processing system, an information processing method, and a program, in which interpretation or utilization of a microbial community or a biomolecule group can be facilitated.

In addition, another object of the aspects of the present invention is to provide an information processing system, an information processing method, and a program capable of exhibiting operational effects disclosed in an embodiment, which will be described below.

Means for Solving the Problem

To solve the above-described problem, one aspect of the present invention is an information processing system including: a sample data acquisition unit that acquires, for each sample, sample data in which a first cluster and a second cluster are associated with each other, the first cluster including a plurality of sets of a biological element detected from the sample and a biological element quantity indicating a quantity of the biological element, the second cluster including a plurality of sets of a morpheme regarding text describing an environment in which the sample is present and an appearance frequency of the morpheme; and a generation unit that analyzes a plurality of pieces of the sample data with the biological element quantity and the appearance frequency as parameters and generates information indicating a relationship between the environment and the first cluster.

In addition, another aspect of the present invention is an information processing method in an information processing system, the information processing method including: a first step of acquiring, for each sample, sample data in which a first cluster and a second cluster are associated with each other, the first cluster including a plurality of sets of a biological element detected from the sample and a biological element quantity indicating a quantity of the biological element, the second cluster including a plurality of sets of a morpheme regarding text describing an environment in which the sample is present and an appearance frequency of the morpheme; and a second step of analyzing a plurality of pieces of the sample data with the biological element quantity and the appearance frequency as parameters and generating information indicating a relationship between the environment and the first cluster.

In addition, another aspect of the present invention is a program in a computer, the program including: a first step of acquiring, for each sample, sample data in which a first cluster and a second cluster are associated with each other, the first cluster including a plurality of sets of a biological element detected from the sample and a biological element quantity indicating a quantity of the biological element, the second cluster including a plurality of sets of a morpheme regarding text describing an environment in which the sample is present and an appearance frequency of the morpheme; and a second step of analyzing a plurality of pieces of the sample data with the biological element quantity and the appearance frequency as parameters and generating information indicating a relationship between the environment and the first cluster.

Effect of the Invention

According to the aspects of the present invention, it is possible to facilitate interpretation or utilization of a microbial community or a biomolecule group.

BRIEF DESCRIPTION OF DRAWINGS

FIG. 5 is a view illustrating a data configuration of natural language description data according to the same embodiment.

FIG. 6 is a view illustrating a data configuration of microbial community structure data according to the same embodiment.

FIG. 15 is a view illustrating an example of scores with respect to search queries computed by the metagenomic information processing system according to the same embodiment.

FIG. 16 is a view illustrating a data configuration of metagenomic data according to the same embodiment.

FIG. 17 is a view illustrating a data configuration of metabolome data according to the same embodiment.

EMBODIMENTS FOR CARRYING OUT THE INVENTION

Hereinafter, an embodiment of the present invention will be described with reference to the drawings.

First Embodiment

[Overview of Metagenomic Information Processing System 1]

A first embodiment of the present invention will be described.

A metagenomic information processing system 1 is an information processing system which assists metagenomic analysis. For example, a sample data pair which becomes an analysis target of the metagenomic information processing system 1 is data in which microbial community structure data (phyletic component data) and natural language description data are associated with each other for each sample of a microbial community. In microbial community structure data, for example, identification information of microbes included in a sample, and numerical information indicating the quantity of the microbes are described. In natural language description data, for example, information of words (character strings) such as environments where samples were acquired, that is, environmental labels indicating habitat environments of microbes, and numerical information indicating the appearance frequency of the words are described.

As described above, the sample according to the present embodiment has an aspect of microbes and an aspect of character strings. As a sample data pair, for example, base sequence data of a metagenomic sample registered in a complementary base sequence database and annotation data describing details and the like of the sample in a natural language can be processed to be used. Hereinafter, a sample data pair before being processed will be referred to as an input sample data pair and a sample data pair after being processed will be referred to as a processed sample data pair.

Figure 1:
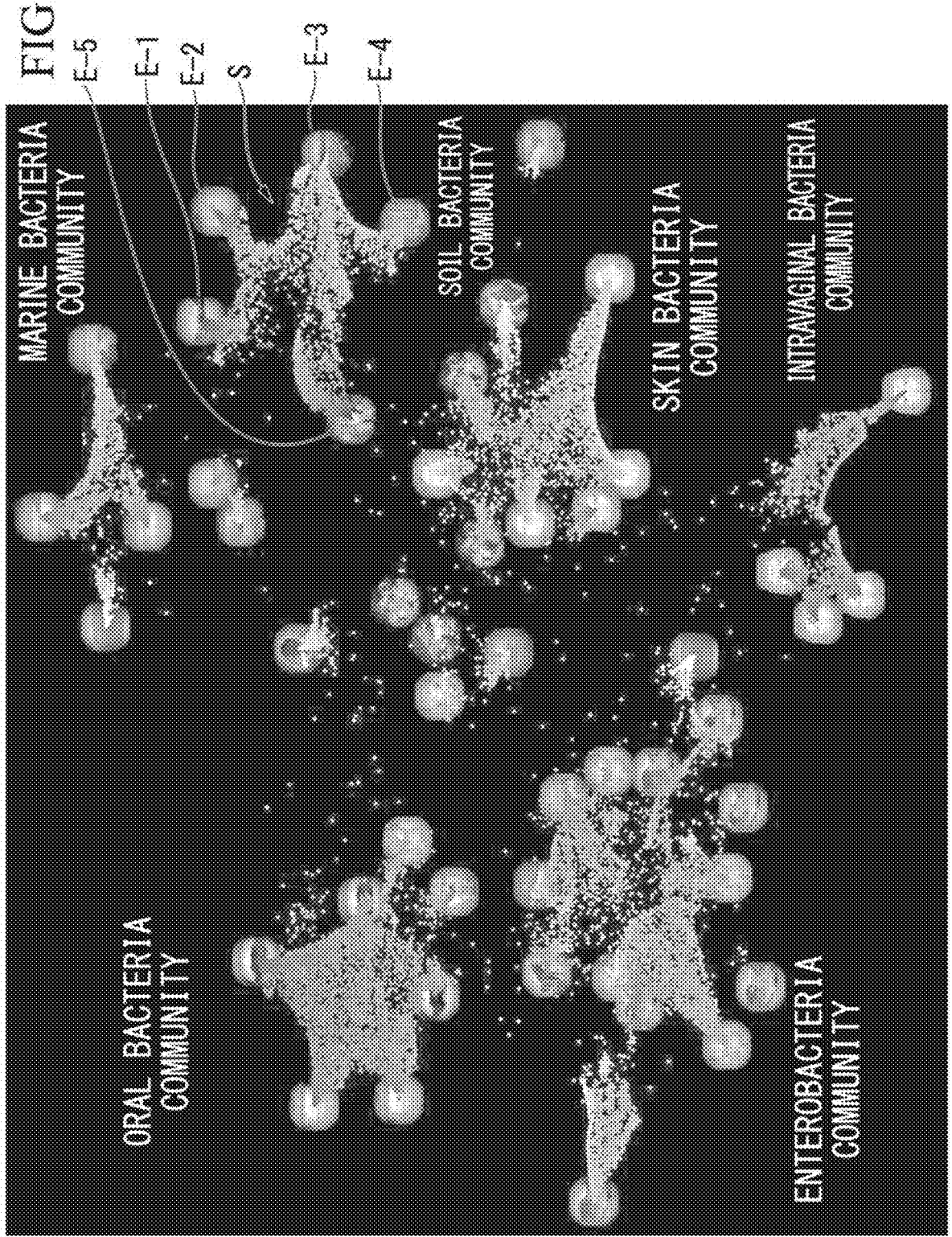
FIG. 1 is a schematic view illustrating an overview of a metagenomic information processing system according to a first embodiment of the present invention.

FIG. 1 is a schematic view illustrating an overview of the metagenomic information processing system 1 according to the present embodiment.

FIG. 1 illustrates an image in which a metagenomic model generated by the metagenomic information processing system 1 is expressed in a two-dimensional plane. This metagenomic model image MD is a probability model (function)

in which a number of samples acquired from natural environments are individually expressed as a linear combination of a plurality of latent environmental factors. In other words, a latent environmental factor is a unit (element) in which a sample can be expressed in a mixture thereof. As described above, since a sample has the aspect of microbes and the aspect of character strings, the latent environmental factor also has the aspect of microbes and the aspect of character strings. That is, the latent environmental factor is a unit (a sub-community or a partial community) of microbial communities and is a unit (a word subset) of character string clusters. Hereinafter, the unit of microbial communities will be referred to as a unit microbial community. In addition, the unit of character string clusters will be referred to as a unit character string cluster.

In the example illustrated in FIG. 1, plots (dots) disposed on a two-dimensional plane individually correspond to the samples, and circles larger than the plots correspond to the latent environmental factors. For example, a sample group S of a soil bacteria community is expressed as a linear combination of five latent environmental factors E-1 to E-5. The position of each of the samples corresponds to the mixture ratio of the latent environmental factors. For example, a sample disposed at a position close to the latent environmental factor E-1 includes the latent environmental factor E-1 at a high proportion.

Through machine learning in which a number of samples are used, the metagenomic information processing system 1 generates a metagenomic model in which all the samples are assumed to be shown in a mixture of the latent environmental factors.

In other words, the metagenomic information processing system 1 acquires the latent environmental factors.

Accordingly, the metagenomic information processing system 1 acquires the latent environmental factors and expresses samples as mixtures of the latent environmental factors. That is, the metagenomic information processing system 1 clarifies the relationship between samples and the latent environmental factors. Thus, the metagenomic information processing system 1 can facilitate interpretation of a sample.

[Constitution of Metagenomic Information Processing System 1]

Next, a constitution of the metagenomic information processing system 1 will be described.

Figure 2:
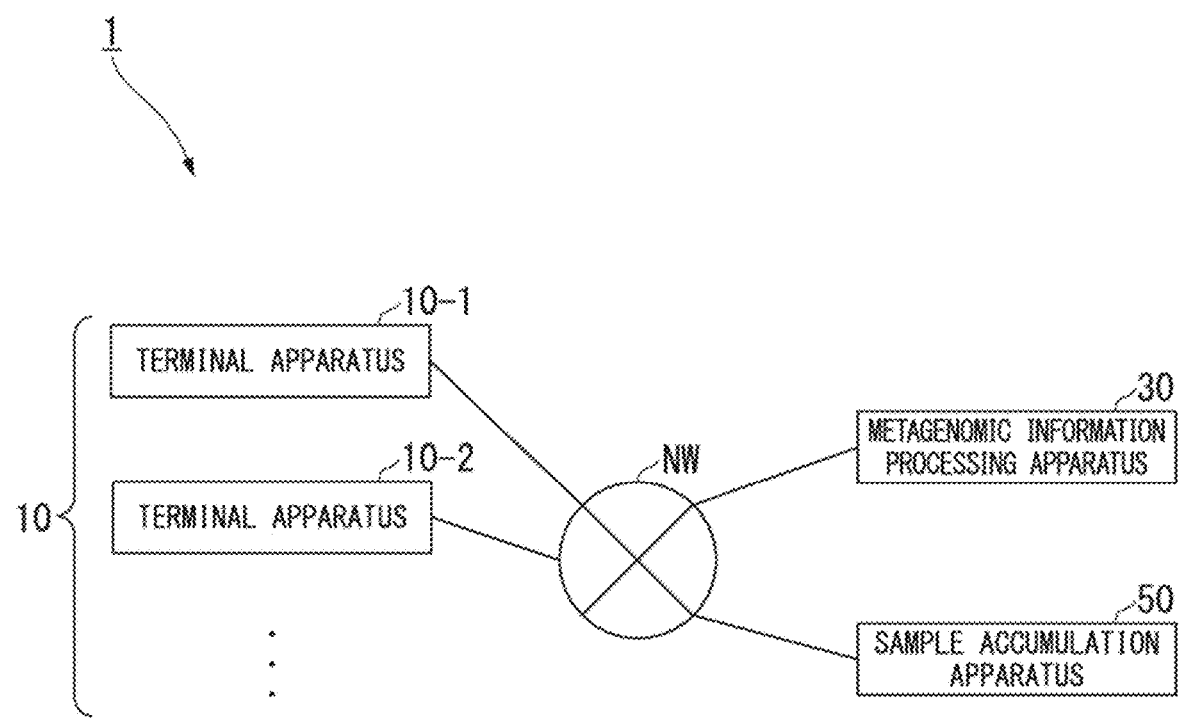
FIG. 2 is a block diagram illustrating a constitution of the metagenomic information processing system according to the same embodiment.

FIG. 2 is a block diagram illustrating a constitution of the metagenomic information processing system 1.

The metagenomic information processing system 1 includes one or more terminal apparatuses 10-1, 10-2, and so on, a metagenomic information processing apparatus 30, and a sample accumulation apparatus 50. Hereinafter, when the terminal apparatuses 10-1, 10-2, and so on are not particularly distinguished from each other, each of the apparatuses will be generally referred to as the terminal apparatus 10. The terminal apparatus 10, the metagenomic information processing apparatus 30, and the sample accumulation apparatus 50 can communicate with each other via a network NW.

The terminal apparatus 10 is an electronic instrument including a computer system. Specifically, the terminal apparatus 10 may be a personal computer, a smartphone, a tablet terminal, a personal handyphone system (PHS) terminal, a portable telephone, or the like.

The terminal apparatus 10 provides a user interface for receiving an operational input from a user or presenting information to a user.

The metagenomic information processing apparatus 30 is an electronic instrument including a computer system. Specifically, the metagenomic information processing apparatus 30 may be a web server or the like. The metagenomic information processing apparatus 30 has a function of acquiring a metagenomic model in which latent environmental factors are assumed to be present, based on input sample data pairs accumulated in the sample accumulation apparatus 50. In addition, the metagenomic information processing apparatus 30 provides a function of predicting (analyzing) a new sample based on the metagenomic model. In addition, the metagenomic information processing apparatus 30 provides a function of searching based on the metagenomic model.

The sample accumulation apparatus 50 is an electronic instrument including a computer system. Specifically, the sample accumulation apparatus 50 may be a web server or the like. A number of input sample data pairs are accumulated in the sample accumulation apparatus 50. For example, the input sample data pairs may be pieces of data contributed (uploaded) by researchers and the like at various places such that the data can be utilized. For example, as the sample accumulation apparatus 50, a complementary base sequence database such as Sequence Read Archive (https://www.ncbi.nlm.nih.gov/sra) may be utilized for public use. The sample accumulation apparatus 50 stores sample data pairs received from another apparatus and transmits sample data pairs to an apparatus of a request source upon request from another apparatus.

[Constitution of Terminal Apparatus 10]

Next, a constitution of the terminal apparatus 10 will be described.

Figure 3:
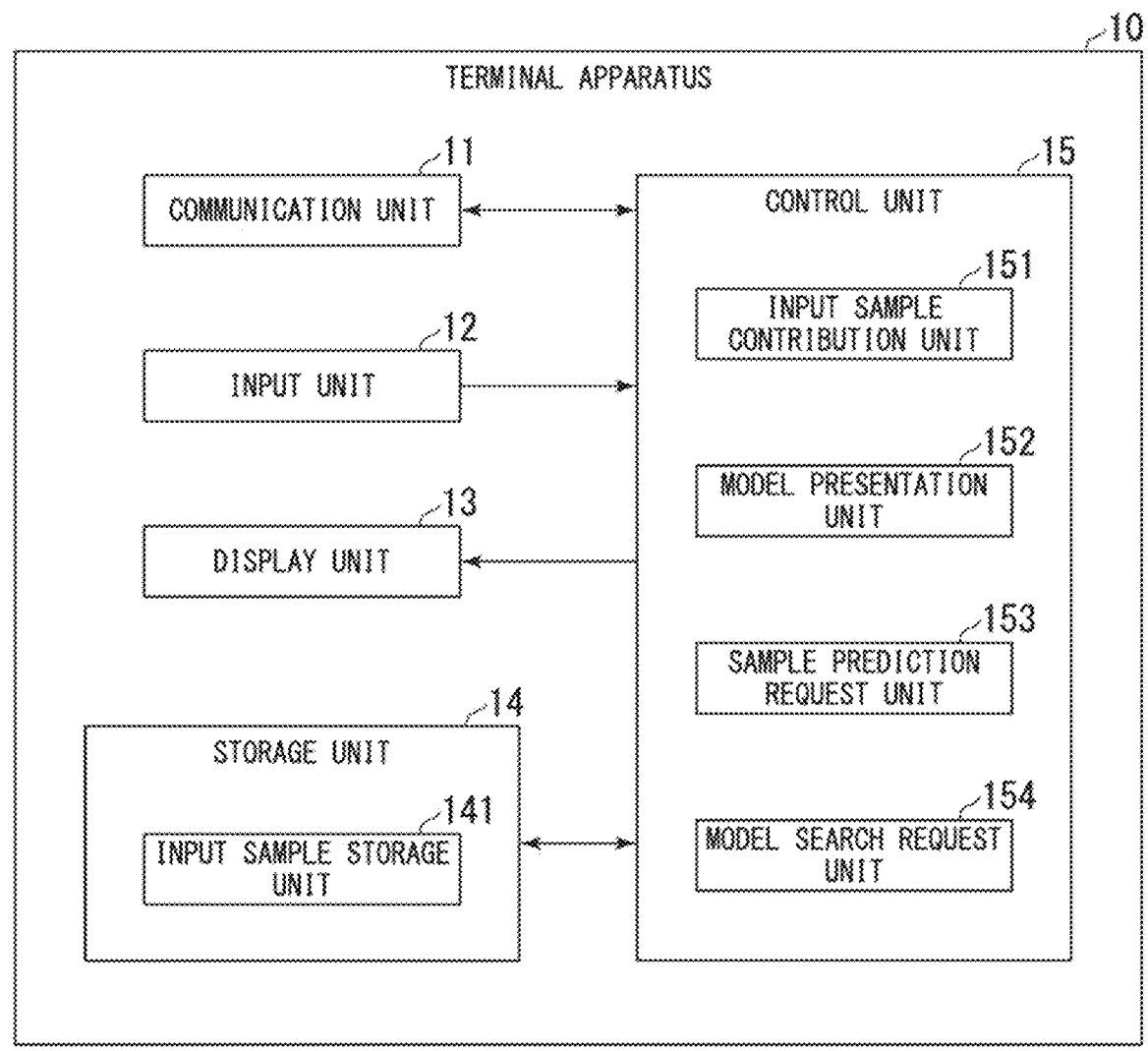
FIG. 3 is a block diagram illustrating a constitution of a terminal apparatus according to the same embodiment.

FIG. 3 is a block diagram illustrating a constitution of the terminal apparatus 10. The terminal apparatus 10 includes a communication unit 11, an input unit 12, a display unit 13, a storage unit 14, and a control unit 15.

The communication unit 11 includes a communication module, which communicates with another apparatus connected to the network NW.

The input unit 12 includes a pointing device such as a mouse and a touch pad, and an input module such as a keyboard, which receive an operational input of a user. The display unit 13 includes a display module such as a liquid crystal display panel, which displays various kinds of information.

The storage unit 14 includes a storage module such as a read only memory (ROM), a random access memory (RAM), a hard disc drive (HDD), or a flash memory, which stores various kinds of data of various kinds of programs and the like executed by a central processing unit (CPU) included in the terminal apparatus 10. The storage unit 14 includes an input sample storage unit 141.

The input sample storage unit 141 stores input sample data pairs.

The control unit 15 controls constituent parts of the terminal apparatus 10. For example, the control unit 15 functions when the CPU of the terminal apparatus 10 executes the program stored in the storage unit 14. In addition, for example, a part or all of the control unit 15 may be an integrated circuit such as an application specific integrated circuit (ASIC). The control unit 15 includes an input sample contribution unit 151, a model presentation unit 152, a sample prediction request unit 153, and a model search request unit 154.

The input sample contribution unit 151 acquires an input sample data pair via the input unit 12 or from the input sample storage unit 141. The input sample storage unit 141 contributes an acquired input sample data pair to the sample accumulation apparatus 50. In other words, the input sample contribution unit 151 transmits an input sample data pair to the sample accumulation apparatus 50 and causes the sample accumulation apparatus 50 to store input sample data pair.

The model presentation unit 152 acquires image data of a metagenomic model (refer to FIG. 1) from the metagenomic information processing apparatus 30. The model presentation unit 152 causes the display unit 13 to display an image of an acquired metagenomic model.

The sample prediction request unit 153 causes the display unit 13 to display a screen for providing a function of prediction using a metagenomic model. The sample prediction request unit 153 receives designation of a sample (analysis target) from a user via the input unit 12. The sample prediction request unit 153 makes a request for prediction using a metagenomic model to the metagenomic information processing apparatus 30 regarding a designated sample. When a prediction result is acquired from the metagenomic information processing apparatus 30, the sample prediction request unit 153 causes the display unit 13 to display the prediction result.

The model search request unit 154 causes the display unit 13 to display a screen for providing a function of searching using a metagenomic model. The model search request unit 154 acquires a search query from a user via the input unit 12. The model search request unit 154 makes a request for searching using a metagenomic model to the metagenomic information processing apparatus 30 based on an acquired search query. When a search result is acquired from the metagenomic information processing apparatus 30, the model search request unit 154 causes the display unit 13 to display the search result.

[Constitution of Metagenomic Information Processing Apparatus 30]

Next, a constitution of the metagenomic information processing apparatus 30 will be described.

Figure 4:
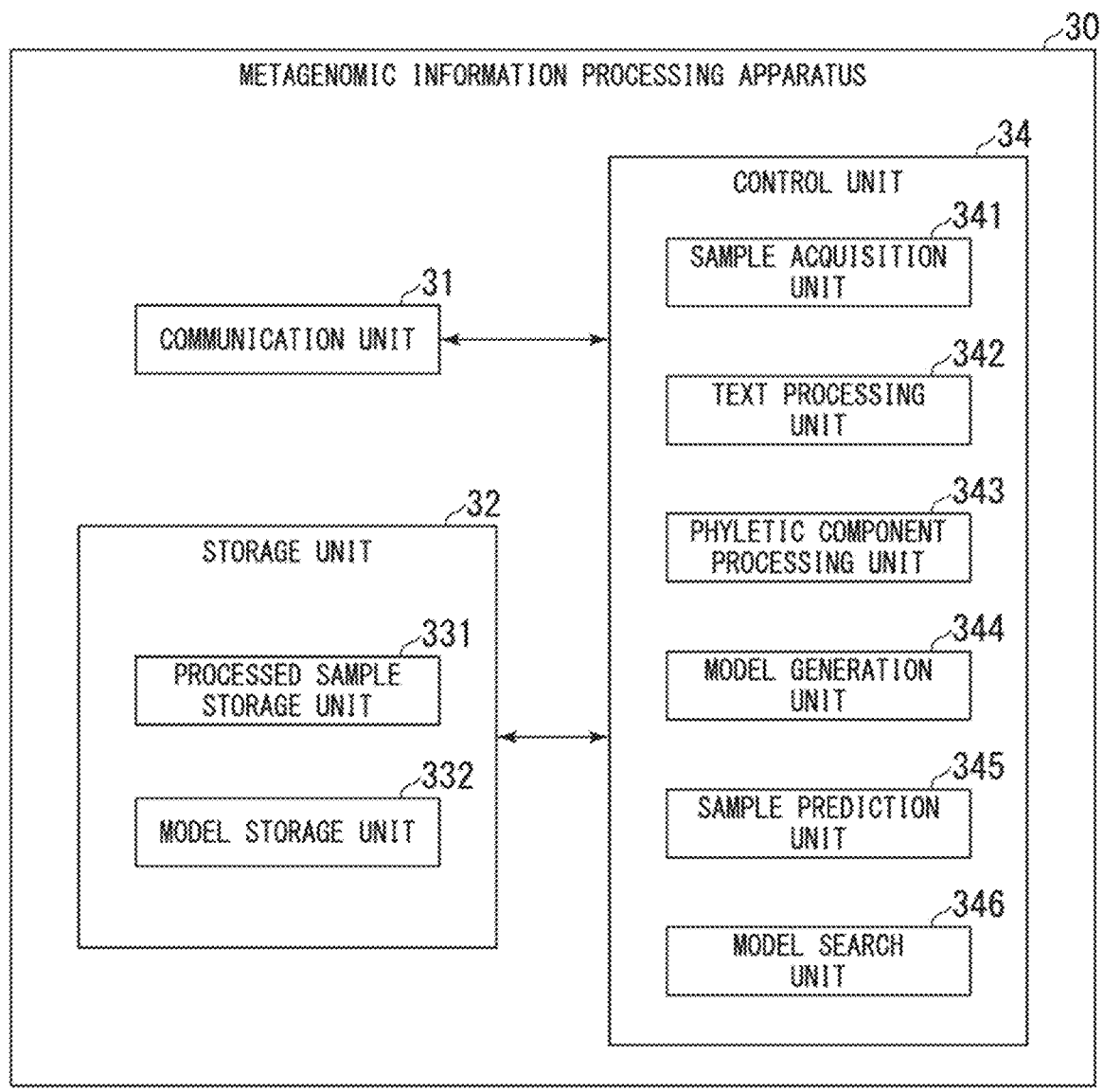
FIG. 4 is a block diagram illustrating a constitution of a metagenomic information processing apparatus according to the same embodiment.

FIG. 4 is a block diagram illustrating a constitution of the metagenomic information processing apparatus 30.

The metagenomic information processing apparatus 30 includes a communication unit 31, a storage unit 32, and a control unit 34.

The communication unit 31 includes a communication module, which communicates with another apparatus connected to the network NW.

The storage unit 32 includes a storage module such as a ROM, a RAM, an HDD, or a flash memory, which stores various kinds of data of various kinds of programs and the like executed by a CPU included in the metagenomic information processing apparatus 30. The storage unit 32 includes a processed sample storage unit 331 and a model storage unit 332.

The processed sample storage unit 331 stores processed sample data pairs. Here, specific examples of natural language description data of the processed sample data pair and microbial community structure data will be described.

FIG. 5 is a view illustrating a data configuration of natural language description data.

In the example illustrated in FIG. 5, the natural language description data is configured to have sample IDs (identifiers), pieces of lexical information, and pieces of appearance frequency information which are associated with each other. The sample ID is information uniquely identifying a sample of a microbial community. The character string information is information indicating a character string of an environmental label or the like. The appearance frequency information is information indicating the appearance frequency of a character string indicated by the character string information. In this manner, the natural language description data is data quantitatively expressing the feature of a sample in a linguistic aspect.

FIG. 6 is a view illustrating an example of microbial community structure data.

In the example illustrated in FIG. 6, the natural language description data is configured to have sample IDs (identifiers), pieces of microbe name information, and pieces of quantitative information which are associated with each other. The sample ID is similar to that in the natural language description data. That is, the natural language description data and the microbial community structure data are associated with each other via the sample ID. The microbe name information is identification information of a microbe. For example, the microbe name information is information indicating the name of a microbe. The quantitative information is information indicating the quantity of the microbe indicated by the microbe name information. In this manner, the microbial community structure data is data quantitatively expressing the feature of a sample in a genetic aspect.

Return to FIG. 4, description of the constitution of the metagenomic information processing apparatus 30 will be continued.

The model storage unit 332 stores data of a metagenomic model.

The control unit 34 controls constituent parts of the metagenomic information processing apparatus 30. For example, the control unit 34 functions when the CPU of the metagenomic information processing apparatus 30 executes the program stored in the storage unit 32. In addition, for example, a part or all of the control unit 34 may be an integrated circuit such as an ASIC. The control unit 34 includes a sample acquisition unit 341, a text processing unit 342, a phyletic component processing unit 343, a model generation unit 344, a sample prediction unit 345, and a model search unit 346.

The sample acquisition unit 341 acquires an input sample data pair or a processed sample data pair from the terminal apparatus 10, the sample accumulation apparatus 50, or the like via the communication unit 31.

The text processing unit 342 processes annotation data of an input sample data pair in a form suitable for generating a metagenomic model and generates natural language description data for a processed sample data pair. Specifically, the text processing unit 342 performs analysis of a morpheme, lemmatization (conversion of a verb into the root form, conversion of a plural form into a singular form, or the like), elimination of unnecessary character strings, and the like. For example, the text processing unit 342 eliminates English stop words, character strings including "_" (underscore) or a colon, uniform resource locators (URLs), character strings including a base sequence (for example, character strings including A, T, C, and G at a predetermined proportion or more), universal words (genome and metagenome) irrelevant to the sample, and the like. In addition, the text processing unit 342 counts the appearance frequency (frequency) of each word.

The phyletic component processing unit 343 generates microbial community structure data for a processed sample data pair with reference to the base sequence data of an input sample data pair. Specifically, the phyletic component processing unit 343 identifies a microbe based on the base sequence described in base sequence data and counts the appearance frequency (the number of leads) of each microbe. For example, a microbe is identified by being associated with the same phyletic taxon. Specifically, the phyletic taxon may be homogenized in the level of the genus or the level of the species.

The model generation unit 344 generates a metagenomic model based on a processed sample data pair. Here, metagenomic model generation processing will be described. In the present embodiment, in order to generate a metagenomic model, learning is performed utilizing "corresponding topic modeling" (Non-Patent Document 2) which is a kind of probability models called topic modeling.

First, it is assumed that D pieces of data are given as data of an analysis target. Boldfaced parameters in the following mathematical expressions express clusters. In addition, for the sake of convenience of description, in regard to the boldfaced parameters in the mathematical expressions in this paper, boldfaced type is indicated in parentheses with respect to the parameters. A cluster of a data pair used for generating a metagenomic model is expressed by the following Expression (1).

[Math. 1]

$$D=(W,T) \qquad (1)$$

A cluster of microbial community structure data is expressed by the following Expression (2).

[Math. 2]

$$W=\{w_d\}_{d=1}^{D} \qquad (2)$$

A cluster of natural language description data is expressed by the following Expression (3).

[Math. 3]

$$T=\{t_d\}_{d=1}^{D} \qquad (3)$$

Each data pair d includes microbial community structure data $w_d$ (boldfaced) and natural language description data $t_d$ (boldfaced). The dth (d=1 to D) data is expressed by the following Expressions (4) to (7).

[Math. 4]

$$w_d=\{w_{dn}\}_{n=1}^{N_d} \qquad (4)$$

$$w_{dn} \in \{1, \ldots, W\} \qquad (5)$$

$$t_d=\{t_{dm}\}_{m=1}^{M_d} \qquad (6)$$

$$t_{dm} \in \{1, \ldots, T\} \qquad (7)$$

In Expression (4), the factor $w_d$ (boldfaced) expresses the microbial community structure data in the processed sample data pair d. When a microbial community consists of a cluster of $N_d$ microbes, the factors $w_{dn}$ of Expressions (4) and (5) express the taxons of the nth microbes in the data pairs d. The factor W in Expression (5) expresses the total number of the kinds of microbes which have appeared in the microbial community structure data. The factor $t_d$ (boldfaced) in Expression (6) expresses the natural language description data in the data pair d. When the character string cluster consists of a cluster of $M_d$ words, the factors $t_{dm}$ of Expressions (6) and (7) express the kinds of the mth words in the character string clusters. The factor T in Expression (7) expresses the total number of the kinds of words (the number of lexicons) which have appeared in the natural language description data.

The latent environmental factor of each piece of data is estimated as "a topic" in corresponding topic modeling. It is assumed that each element in data, such as a word which has appeared in the data, has a latent topic in topic modeling.

The cluster Z (boldfaced) of the topic where the microbial community structure data belongs is expressed by the following Expression (8).

[Math. 5]

$$Z=\{\{z_{dn}\}_{n=1}^{N_d}\}_{d=1}^{D} \qquad (8)$$

In Expression (8), the factor $z_{dn}$ expresses the topic of the nth microbe of the dth microbial community structure data.

[Math. 6]

$$z_{dn} \in \{1, \ldots, Z\} \qquad (9)$$

In Expression (9), the factor Z expresses the total number of topics, that is, the total number of latent environmental factors set in advance.

The natural language description data of each piece of data individually has a latent topic as well. The cluster C (boldfaced) of the topic where the natural language description data belongs is expressed by the following Expression (10).

[Math. 7]

$$C=\{\{c_{dm}\}_{m=1}^{M_d}\}_{d=1}^{D} \qquad (10)$$

In Expression (10), the factor $c_{dm}$ expresses the topic of the mth word of the dth natural language description data.

[Math. 8]

$$c_{dm} \in \{1, \ldots, Z\} \qquad (11)$$

In Expression (11), the topic of the natural language description data also has the same topic number Z as the topics of the microbial community structure data. In the case of $z_{dn}=c_{dm}$, it is assumed that the nth microbe of the dth data and the mth word of the dth data belong to the same topic, that is, the same latent environmental factor. The factors Z and C are unknown parameters inferred from the data.

Regarding the entire data set, the inference of the unknown parameters is determined as parameters when a likelihood expressed by the following Expression (12) is calculated and the likelihood is maximized by some sort of optimized calculation regarding a simultaneous probability distribution related to the microbial community structure data W (boldfaced), the natural language description data T (boldfaced), the latent topic (unit microbial community) Z (boldfaced) of the microbial community, and the latent topic (unit character string cluster) C (boldfaced) of the natural language.

[Math. 9]

$$P(W,T,Z,C|\alpha,\beta,\gamma)=P(Z|\alpha)P(W|Z,\beta)P(C|Z)P(T|C,\gamma) \qquad (12)$$

In Expression (12), the factor $P(\bullet)$ expresses the probability distribution.

The probability distribution P (Z (boldfaced)|α) of the first member on the right side in Expression (12) is expressed by Expression (13), expressing an assumption that topics which appear in the data are generated in accordance with multinomial distributions $\theta_d$ to Dirichlet (α(boldfaced)) in which the Dirichlet distribution having $\alpha_z$ (z=1 to Z) as a hyperparameter becomes a prior distribution.

[Math. 10]

$$P(Z|\alpha)=\pi_{d=1}^{D}\int P(z_d|\theta_d)P(\theta_d|\alpha)d\theta_d \qquad (13)$$

In Expression (13), the factor $\theta_d$ (boldfaced) (d=1 to D) expresses the multinomial distribution which is a generation probability of the topic in the data pair d. The following Expression (14) is obtained by integrating and deleting the factor $\theta_d$ (boldfaced) of Expression (13).

[Math. 11]

$$P(Z \mid \alpha) = \left(\frac{\Gamma(\sum_{z=1}^{Z} \alpha_z)}{\prod_{z=1}^{Z} \Gamma(\alpha_z)}\right)^D \prod_{d=1}^{D} \frac{\prod_{z=1}^{Z} \Gamma(N_{zd} + \alpha_z)}{\Gamma(N_d + \sum_{z=1}^{Z} \alpha_z)} \quad (14)$$

In Expression (14), the factor $\tau(\bullet)$ expresses the gamma function. The factor $N_{zd}$ expresses the number of microbes to which the topics z are assigned in the data pair d.

The probability distribution P (W (boldfaced)|Z (boldfaced) and β) of the second member on the right side in Expression (12) is expressed by the following Expression (15), expressing an assumption that the microbes in the microbial community structure data are generated in accordance with multinomial distributions $\varphi_z$ to Dirichlet (β) in which the Dirichlet distribution having the hyperparameter β becomes a prior distribution, when the latent topic thereof is z. Expression (15) is obtained by performing integration and deletion similar to those in Expression (14).

[Math. 12]

$$P(W \mid Z, \beta) = \left(\frac{\Gamma(\beta W)}{\Gamma(\beta)^W}\right)^Z \prod_{z=1}^{Z} \frac{\prod_{w=1}^{W} \Gamma(N_{zw} + \beta)}{\Gamma(N_z + \beta W)} \quad (15)$$

In Expression (15), the factor $N_{zw}$ expresses the number of topics z assigned to the microbes w. The factor $N_z$ expresses the number of microbes to which the topics z are assigned in the entire data set.

The probability distribution P (C (boldfaced)|Z (boldfaced)) of the third member on the right side in Expression (12) is expressed by Expression (16), expressing an assumption that the words in the natural language description data are generated based on a multinomial distribution having the same proportion as the distribution of the topics assigned to the microbial community structure data.

[Math. 13]

$$P(C \mid Z) = \prod_{d=1}^{D} \prod_{z=1}^{Z} \left(\frac{N_{zd}}{N_d}\right)^{M_{zd}} \quad (16)$$

In Expression (16), the factor $M_{zd}$ expresses the number of words in the natural language description data to which the topics z are assigned in the data pair d.

The probability distribution P (T (boldfaced)|C (boldfaced) and γ) of the fourth member on the right side in Expression (12) is expressed by Expression (17), expressing an assumption that the words in the natural language description data are generated in accordance with multinomial distributions $\phi_c$ to Dirichlet (γ) in which the Dirichlet distribution having the hyperparameter γ becomes a prior distribution, when the latent topic thereof is c. Expression (17) is obtained by performing integration and deletion similar to those in Expression (14).

[Math. 14]

$$P(T \mid C, \gamma) = \left(\frac{\Gamma(\gamma T)}{\Gamma(\gamma)^T}\right)^Z \prod_{z=1}^{Z} \frac{\prod_{t=1}^{T} \Gamma(M_{zt} + \gamma)}{\Gamma(M_z + \gamma T)} \quad (17)$$

In Expression (17), the factor $M_{zt}$ expresses the number of topics z assigned to the words t. The factor $M_z$ expresses the number of words to which the topics z are assigned in the entire data set.

In the present embodiment, posterior distributions regarding the latent topics Z (boldfaced) of the microbial community structure data and the latent topics C (boldfaced) of the natural language description data included in the foregoing expressions are inferred through collapse Gibbs sampling which is a kind of a Markov chain Monte Carlo method.

First, the latent topics of the elements of the microbial community structure data and the natural language description data in the entire data set are randomly initialized in a uniform distribution having z□{1 and so on to Z} as elements.

In each step of the Gibbs sampling, in accordance with the following Expressions (18) and (19), the latent topics of the elements of the microbial community structure data and the natural language description data are sampled. The steps of the Gibbs sampling are repeated until the simultaneous likelihood of Expression (12) is converged.

Regarding the microbial community structure data, the sampling probability of the latent topic z of the nth microbe in the data pair d is expressed by Expression (18).

[Math. 15]

$$P(z_{dn} = k \mid W, T, Z_{\backslash dn}, C) \propto (N_{kd\backslash dn} + \alpha_k) \frac{N_{kw_{dn}\backslash dn} + \beta}{N_{k\backslash dn} + \beta W} \left(\frac{N_{kd\backslash dn} + 1}{N_{kd\backslash dn}}\right)^{M_{kd}} \quad (18)$$

Hereinafter, for the sake of convenience of description, a backslash in the mathematical expressions will be marked as a slash (/) in this paper. In Expression (18), the factor Z (boldfaced)$_{/dn}$ indicates a cluster obtained by excluding the topic of the nth microbe in the data pair d from the topic cluster Z (boldfaced). The factor $N_{kd/dn}$ expresses the number of microbes assigned to the topics k regarding the microbes from which the nth microbe in the data pair d is excluded, when the factor $z_{dn}$ is k. The factor $N_{kwdn/dn}$ expresses the number of microbes $w_{dn}$ assigned to the topics k in the factor Z (boldfaced)$_{/dn}$, when the factor $z_{dn}$ is k. The factor $N_{k/dn}$ expresses the number of topics k in the factor Z (boldfaced)$_{/dn}$, when the factor $z_{dn}$ is k.

Regarding the natural language description data, the sampling probability of the latent topic c of the nth word in the data pair d is expressed by Expression (19).

[Math. 16]

$$P(c_{dm} = k \mid W, T, C_{\backslash dm}, Z) \propto N_{kd} \frac{M_{kt_{dm}\backslash dm} + \gamma}{M_{k\backslash dm} + \gamma T} \quad (19)$$

In Expression (19), the factor C (boldfaced)$_{/dm}$ indicates a cluster obtained by excluding the topic of the mth word in the data pair d from the topic cluster C (boldfaced). The factor $N_{kd}$ expresses the number of microbes assigned to the topics k in the data pair d, when the factor $c_{dm}$ is k. The factor $M_{ktdm/dm}$ expresses the number of words $t_{dm}$ assigned to the topics k in the factor C (boldfaced)$_{/dm}$, when the factor $c_{dm}$ is k. The factor $M_{d/dm}$ expresses the number of topics k in the factor C (boldfaced)$_{/dm}$, when the factor $c_{dm}$ is k.

In the present embodiment, an asymmetrical Dirichlet distribution is employed as the Dirichlet distribution which is a prior distribution of a topic generation multinomial distribution of the microbial community structure data, and the hyperparameter α is varied for each topic. Since samples whose microbial community structures have been analyzed in previous studies are significantly biased to those acquired from the inside of the human gut, and it is presumed that significant bias may also be present in the appearance probability of a latent topic in the entire data set, the foregoing procedure is performed to achieve a model suitable for such bias. Suitable initial values are set to Z hyperparameters α and hyperparameters β and γ and are updated in accordance with the following Expressions (20) to (22) in each step of the Gibbs sampling.

[Math. 17]

$$\alpha_k \leftarrow \hat{\alpha_k} \frac{\sum_{d=1}^{D} \Psi(N_{zd} + \hat{\alpha_k}) - D\Psi(\hat{\alpha_k})}{\sum_{d=1}^{D} \Psi(N_d + \sum_{z=1}^{Z} \alpha_z) - D\psi(\sum_{z=1}^{Z} \alpha_z)} \quad (20)$$

$$\beta \leftarrow \hat{\beta} \frac{\sum_{z=1}^{Z} \sum_{w=1}^{W} \Psi(N_{zw} + \hat{\beta}) - ZW\Psi(\hat{\beta})}{W(\sum_{z=1}^{Z} \Psi(N_z + \hat{\beta}W) - Z\Psi(\hat{\beta}W))} \quad (21)$$

$$\gamma \leftarrow \hat{\gamma} \frac{\sum_{z=1}^{Z} \sum_{t=1}^{T} \Psi(M_{zt} + \hat{\gamma}) - ZT\Psi(\hat{\gamma})}{T(\sum_{z=1}^{Z} \Psi(M_z + \hat{\gamma}T) - Z\Psi(\hat{\gamma}T))} \quad (22)$$

In Expressions (20), (21), and (22), the factors $\psi(\bullet)$ express digamma functions defined by Expression (23).

[Math. 18]

$$\Psi(x) = \frac{\partial \log \Gamma(x)}{\partial x} \quad (23)$$

In addition, the hyperparameters marked with "^" in Expressions (20), (21), and (22) are values one step ahead of the Gibbs sampling.

In the stage in which the simultaneous likelihood expressed by Expression (12) is converged by iterative computation through the Gibbs sampling having a sufficient number of steps, the topic generation probability for each sample, that is, the mixture ratio $\theta_{dz}$ of the latent environmental factors is estimated by Expression (24). The microbial occurrence probability for each topic, that is, the constitution $\varphi_{zw}$ of the sub-community of the microbial community for each latent environmental factor is estimated by Expression (25). The word occurrence probability for each topic, that is, the natural language description data generation probability $\varphi_{zt}$ for each latent environmental factor is estimated by Expression (26).

[Math. 19]

$$\theta_{dz} = \frac{N_{zd} + \alpha_z}{N_d + \sum_{z=1}^{Z} \alpha_z} \quad (24)$$

-continued $$\phi_{zw} = \frac{N_{zw} + \beta}{N_z + \beta W} \quad (25)$$

$$\psi_{zt} = \frac{M_{zt} + \gamma}{M_z + \gamma T} \quad (26)$$

Through the foregoing computation processing, regarding all the samples included in the data pairs, the mixture ratio of the latent environmental factors is estimated for each sample, that is, each sample is expressed as a Z-dimensional real-valued vector. The computation results are stored in the model storage unit 332.

Next, a technique of visualizing the data pairs expressed with these Z-dimensional real-valued vectors and executing comparative analysis between samples in a Z-dimensional space will be described.

For visualizing a Z-dimensional real-valued vector, it is effective to perform a technique of disposing sample points within a two-dimensional space or a three-dimensional space using some sort of dimension reduction technique, and it is possible to apply various dimension reduction techniques such as principal component analysis and a multi-dimensional scaling method. Here, an example will be described regarding a case of employing t-distributed stochastic neighbor embedding (t-SNE) (Non-Patent Document 3) that is a technique in which sample points can be embedded in a low dimensional space while a local relationship between the sample points in a high dimensional space is maintained.

In t-SNE, first, a Euclidean distance between sample points within a high dimensional space is converted into a conditional probability expressing the similarity between the sample points. The conditional probability $p_{j|i}$ of the sample point i with respect to the sample point j is expressed by the following Expression (27) in consideration of the normal distribution about the sample point i.

[Math. 20]

$$p_{j|i} = \frac{\exp(-\|x_i - x_j\|^2 / 2\sigma_i^2)}{\sum_{k \neq j} \exp(-\|x_l - x_k\|^2 / 2\sigma_i^2)} \quad (27)$$

The factors $x_i$ and $x_j$ in Expression (27) respectively express the coordinates of the sample points i and j in a high dimensional space, and the factor $\sigma_i$ is a parameter expressing dispersion of the normal distribution about the factor $x_i$. In addition, the factor $\|\bullet\|$ in Expression (27) expresses a Euclidean norm between the sample points $x_i$ and $x_j$.

Moreover, in order to cope with outliers present in the sample, the conditional probability is symmetrized and the simultaneous probability of the sample points $x_i$ and $x_j$ is defined by the following Expression (28).

[Math. 21]

$$p_{ij} = \frac{p_{j|i} + p_{i|j}}{2n} \quad (28)$$

The factor n in Expression (28) expresses the total number of sample points.

A similar simultaneous probability can be defined for the points i and j within a low dimensional space. In t-SNE, in order to appropriately cope with the volume difference between a low dimensional space and a high dimensional space, a t-distribution having a heavier tail than a normal distribution is handled instead of the normal distribution regarding the simultaneous probability between sample points within a low dimensional space. Accordingly, it is possible to further lengthen the distance between the sample points within a low dimensional space, being at a distance from each other in a high dimensional space. When the coordinates of the sample points i and j in a low dimensional space are $y_i$ and $y_j$, the simultaneous probability $q_{ij}$ of the sample points i and j is defined by Expression (29).

[Math. 22]

$$q_{ij} = \frac{(1 + \|y_i - y_j\|^2)^{-1}}{\sum_{k \neq l}(1 + \|y_k - y_l\|^2)^{-1}} \quad (29)$$

The coordinate y (boldfaced) in a low dimensional space is determined by minimizing the loss function expressed by the following Expression (30).

[Math. 23]

$$C = KL(P \| Q) = \sum_{i \neq j} p_{ij} \log \frac{p_{ij}}{q_{ij}} \quad (30)$$

The factor $KL(P\|Q)$ in Expression (30) expresses Kullback-Leibler information divergence between the simultaneous probabilities p and q.

The coordinate y in a low dimensional space obtained by minimizing Expression (30) is expressed in a manner of retaining the features of the distance between samples in a high dimensional space as much as possible.

Here, in a technique of obtaining coordinates in a low dimensional space through directly performed optimized calculation of Expression (30), when Z-dimensional expression of a new sample is predicted and is compared to the existing sample, optimized calculation has to be performed again for the entire data set including the new sample. In this case, there is a possibility that the coordinates of all the samples in a low dimensional space will change every time a new sample is input.

Therefore, the present embodiment employs a technique in which the coordinates in a low dimensional space using only a single sample can be identified by approximating the function having the same behavior as t-SNE in which the Z-dimensional real-valued vector is input and two-dimensional coordinates are output, through a neural network. This technique is proposed in Non-Patent Document 4 and is referred to as parametric t-SNE. The coordinates of the existing sample in a low dimensional space are fixed and only the coordinates of a new sample in a low dimensional space are calculated by this technique. Therefore, the calculation cost can be reduced.

When coordinate conversion from a high dimensional space to a low dimensional space through a feedforward neural network is the function f: X→Y, the simultaneous probability of the sample points i and j in a low dimensional space is expressed by Expression (31).

[Math. 24]

$$q_{ij} = \frac{(1 + \|f(x_i \mid W) - f(x_j \mid W)\|^2)^{-1}}{\sum_{k \neq l}(1 + \|f(x_k \mid W) - f(x_l \mid W)\|^2)^{-1}} \quad (31)$$

In Expression (31), the factor W (boldfaced) is a cluster of weights in the neural network.

The weights in the neural network are learned by performing optimized calculation such as a mini-batch stochastic gradient descent method in which a learning rate is appropriately set while applying Expression (30) as a loss function similar to ordinary t-SNE.

In Non-Patent Document 4, prior learning is individually performed for four restricted Boltzmann machines, and the entire feedforward neural networks are configured by stacking the results thereof. In the present embodiment, as an example, four layers of feedforward neural networks are more conveniently configured, and activation functions of nodes in all layers excluding the fourth layer are subjected to nonlinear conversion as rectified linear units (ReLUs), so that the weights are learned by applying the mini-batch stochastic gradient descent method using all the existing samples without performing prior learning.

Consequently, it is possible to generate an image in which each processed sample data pair is disposed in a two-dimensional plane.

Return to FIG. 4, description of the constitution of the metagenomic information processing apparatus 30 will be continued.

The sample prediction unit 345 performs prediction (analysis) of the mixture ratio of the latent environmental factors in a new sample using a metagenomic model generated by the model generation unit 344. The sample prediction unit 345 acquires the microbial community structure data of the new sample from the terminal apparatus 10. The sample prediction unit 345 estimates the mixture ratio of the latent environmental factors in the new sample utilizing the hyperparameter α of the topic generation probability of the metagenomic model and the microbial occurrence probability φ for each topic.

The sample prediction unit 345 estimates the mixture ratio of the latent environmental factors in the new sample through Gibbs sampling. The sample prediction unit 345 performs sampling in accordance with the following Expression (32) indicating the occurrence probability of the microbe w when the factor $z_{dn}$ (latent topic z) is k, regarding the nth microbe w included in the microbial community structure data of the data pair d of the new sample.

[Math. 25]

$$p(z_{dn} = k \mid W, Z_{dn}, \phi, \alpha) \propto \phi_{kw} \frac{N_{kd \backslash dn} + \alpha_k}{N_{d \backslash dn} + \sum_{z=1}^{Z} \alpha_z} \quad (\text{Expression 32})$$

In Expression (32), the factor $\varphi_{kw}$ is a parameter learned using the existing sample by Expression (25), and the factor $\alpha_k$ is a hyperparameter of the topic generation probability learned using the existing sample. In addition, in Expression (32), the factor $N_{kd/da}$ expresses the number of microbes assigned to the topics k regarding the microbes from which the nth microbe in the data pair d is excluded, and the factor $N_{d/dn}$ expresses the number obtained by subtracting 1 from the total number of microbes included in the data pair d.

After a sufficient number of times of iterative Gibbs sampling computation are executed, the mixture ratio of the latent environmental factor of the new sample is identified through calculation of Expression (24).

The latent environmental factor of the new sample is expressed as the Z-dimensional real-valued vector and is converted into coordinates in a low dimensional space through the feedforward neural network learned from the existing sample. Since they are disposed in the same two-dimensional plane as the existing sample using the converted coordinates, the new sample can be compared to all the existing samples.

The model search unit 346 executes searching using the metagenomic model generated by the model generation unit 344. During searching, the model generation unit 344 utilizes the generation probability $\phi$ of the natural language description data in each of the latent environmental factors and the mixture ratio $\theta$ of the latent environmental factors in each of the processed sample data pairs. The search query may be an arbitrary character string such as one or more words or a sentence.

First, the search query is divided into words, and a search word cluster q (boldfaced)=$\{q_n\}$(n=1 to N) is configured. Thereafter, the model search unit 346 calculates the score of each of the processed sample data pairs used in learning. The score of processed sample data pair d is calculated by the following Expression (33).

[Math. 26]

$$\text{Score}(d)=P(q|d)=\pi_{n=1}^{N}\Sigma_{z=1}^{Z}P(q_n|z)P(z|d)=\pi_{n=1}^{N}\Sigma_{z=1}^{Z}\psi_{zq_n}\theta_{dz} \quad \text{(Expression 33)}$$

That is, the probability that the processed sample data pair d generates the search query q becomes the score. The model search unit 346 outputs information described in the processed sample data pair d having a high score, as the search result.

[Operation of Metagenomic Information Processing System 1]

Next, an operation of the metagenomic information processing system 1 will be described.

First, an operation of the metagenomic information processing system 1 generating a metagenomic model will be described.

Figure 7:
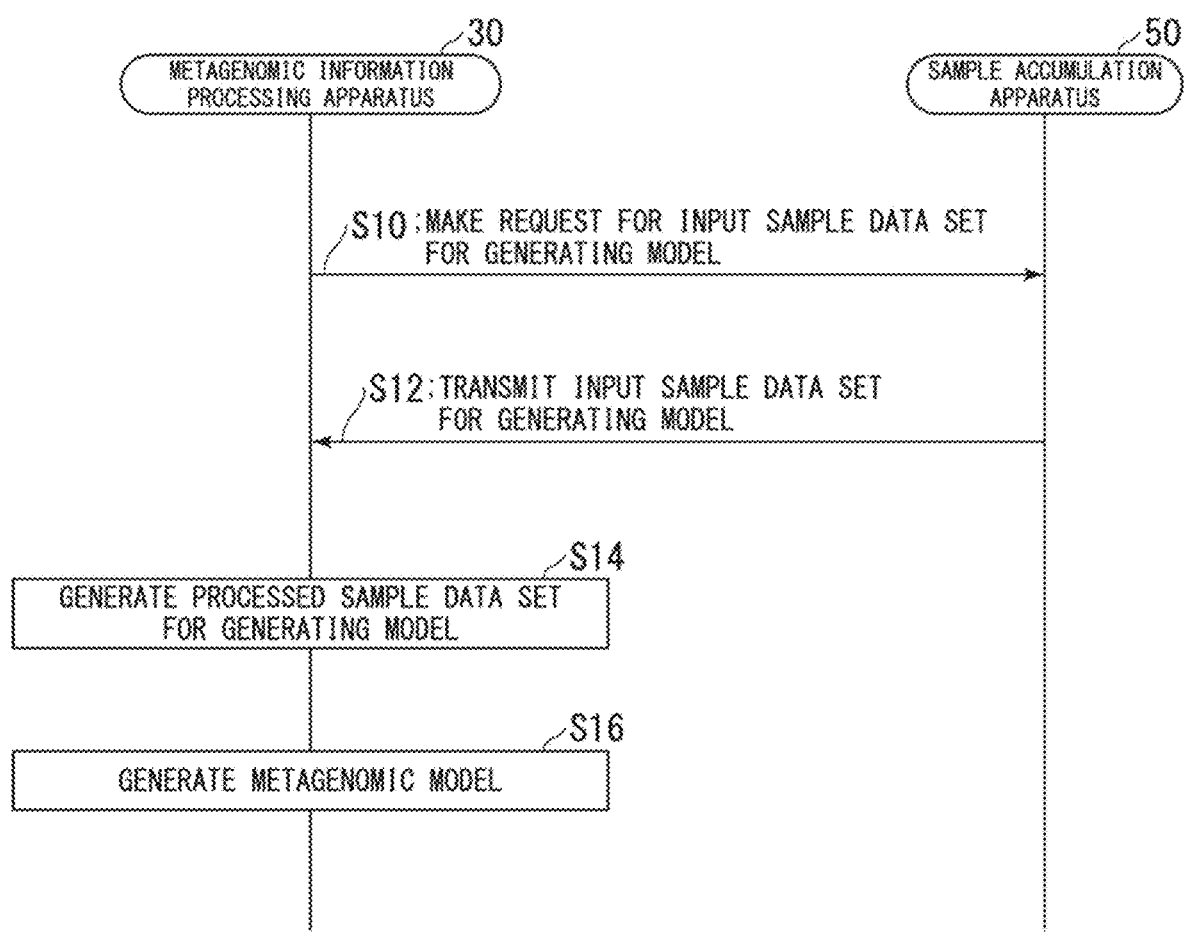
FIG. 7 is a sequence chart illustrating a flow of metagenomic model generation processing of the metagenomic information processing system according to the same embodiment.

FIG. 7 is a sequence chart illustrating a flow of metagenomic model generation processing of the metagenomic information processing system 1.

(Step S10) The metagenomic information processing apparatus 30 makes a request for input sample data pairs to be used for generating a metagenomic model from the sample accumulation apparatus 50. Here, the metagenomic information processing apparatus 30 makes a request for a number of input sample data pairs which is the quantity sufficient to generate the metagenomic model. Thereafter, the metagenomic information processing system 1 proceeds to Step S12 with the processing.

(Step S12) The sample accumulation apparatus 50 transmits the input sample data pair to the metagenomic information processing apparatus 30. Thereafter, the metagenomic information processing system 1 proceeds to Step S14 with the processing.

(Step S14) The metagenomic information processing apparatus 30 generates a processed sample data pair from the input sample data pair acquired from the sample accumulation apparatus 50. Thereafter, the metagenomic information processing system 1 proceeds to Step S16 with the processing.

(Step S16) The metagenomic information processing apparatus 30 performs learning using the processed sample data pair and generates the metagenomic model. Thereafter, the metagenomic information processing system 1 ends the processing illustrated in FIG. 7.

The terminal apparatus 10 can display the latent environmental factor of the metagenomic model generated through the processing in FIG. 7. Here, specific examples of displaying of the latent environmental factors will be described with reference to FIGS. 1, 8, and 9.

In the example illustrated in FIG. 1, the metagenomic model image MD is a model generated based on approximately 30,000 metagenomic samples acquired from a sequence read archive (SRA). Regarding the base sequence data included in each sample, annotation is performed in the phyletic taxon at the genus level, and the result is converted into microbial community structure data. In addition, description data related to the sample including "Description" of the SRA is acquired and is converted into natural language description data (bag of words) for each sample through the processing. The latent environmental factors are extracted using the processed sample data pairs after conversion, and mapping (space filling) is performed in a two-dimensional plane.

Each sample is disposed in accordance with similarity of the mixture ratio of the latent environmental factors. Therefore, the mixture ratios of the latent environmental factors are similar to each other between samples close to each in the metagenomic model image MD. In addition, here, in the coordinates obtained by inputting one hot vector (a real-valued vector in which a certain latent environmental factor is 1 and the remaining latent environmental factors become zero) to a coordinate conversion function established as described above, a photograph corresponding to the latent environmental factor is mapped simultaneously. Therefore, the sample present at a position close to the latent environmental factor means that the sample has an extremely high mixture ratio of the latent environmental factors.

It is possible to extract information such as the kind of latent environmental factors which may be able to be mixed or the kind of environments between which microbial community structures having intermediate properties may be able to be observed, by observing the metagenomic model image MD. Six large clusters (a marine bacteria community, a soil bacteria community, a skin bacteria community, an oral bacteria community, an intravaginal bacteria community, and an enterobacteria community) to which labels are applied for the sake of convenience in the metagenomic model image MD are independent from each other, and a sample having intermediate properties between the clusters is seldom present. Meanwhile, the properties of the samples continuously shift in each of the clusters. For example, within the cluster of the soil bacteria community, the samples continuously shift from a soil factor E-3 to a forest factor E-4 or from the soil factor E-3 to a river factor E-1.

A display of the metagenomic model image MD may be mounted as an interactive web application.

Figure 8:
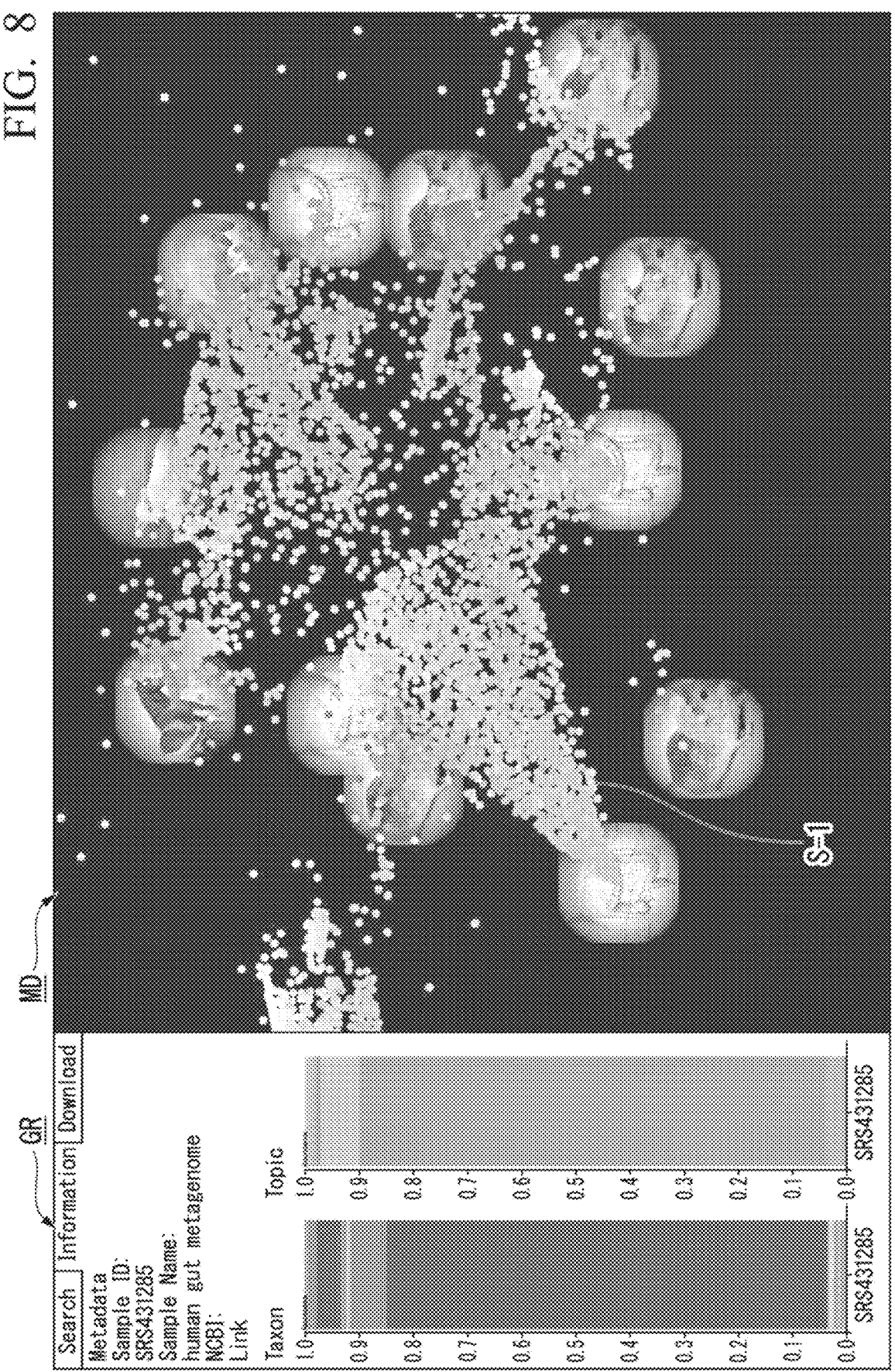
FIG. 8 is a view illustrating a first example of a display screen of the metagenomic information processing system according to the same embodiment.
Figure 9:
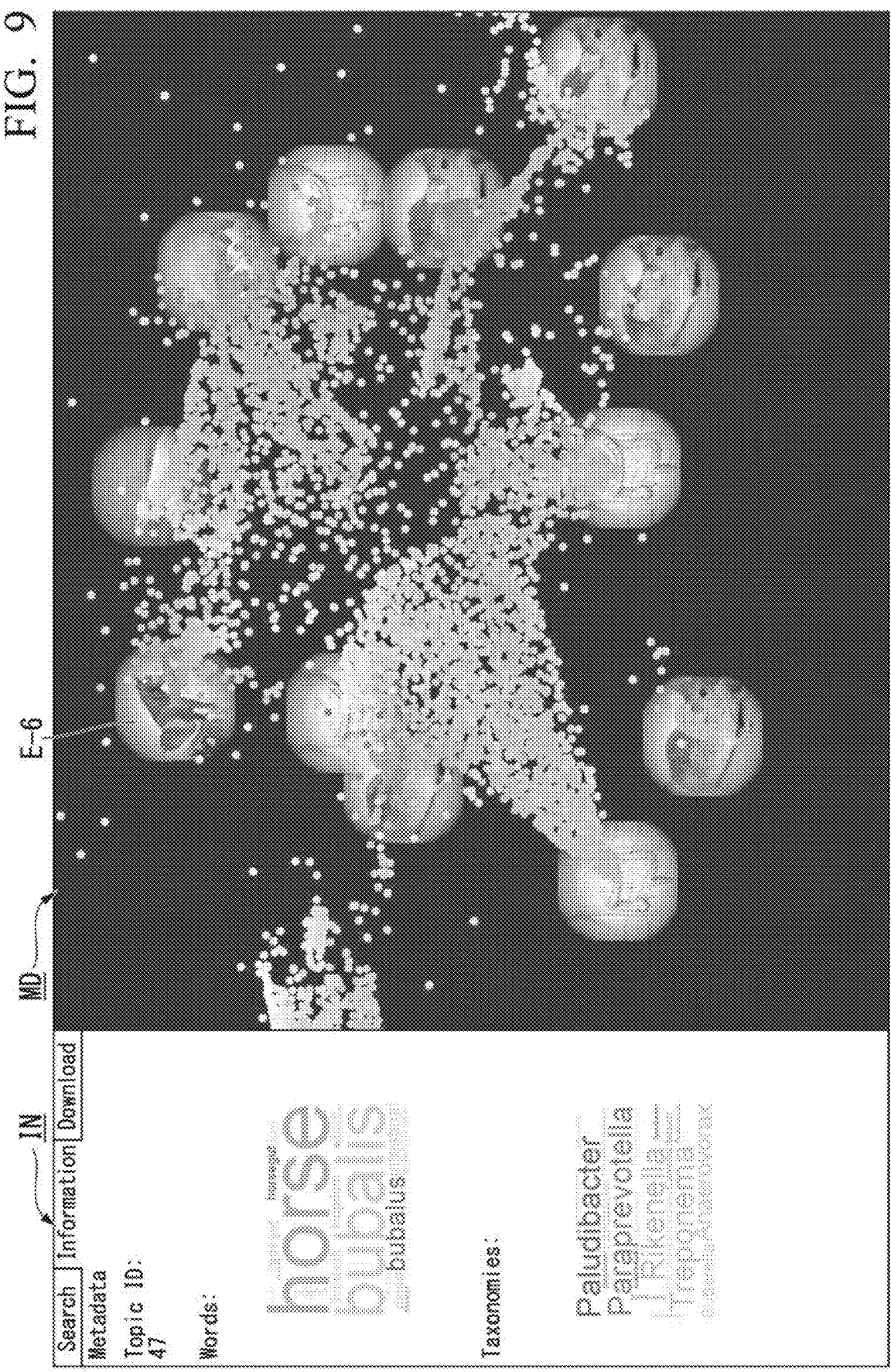
FIG. 9 is a view illustrating a second example of the display screen of the metagenomic information processing system according to the same embodiment.

For example, in the metagenomic model image MD, when a plot (for example, S-1) of the sample is clicked, the metagenomic information processing system 1 may present information related to the sample by changing the display to that in FIG. 8, displaying the microbial community structure of the sample and the mixture ratio of the latent environmental factors in a bar graph GR, or the like. In addition, when the latent environmental factor (for example, E-6) is clicked, the metagenomic information processing system 1 may present information related to the latent environmental factors by changing the display to that in FIG. 9, displaying the generation probability of words corresponding to the factor and a microbial community IN, or the like.

Next, an operation of the metagenomic information processing system 1 predicting the latent environmental factor of a new sample will be described.

Figure 10:
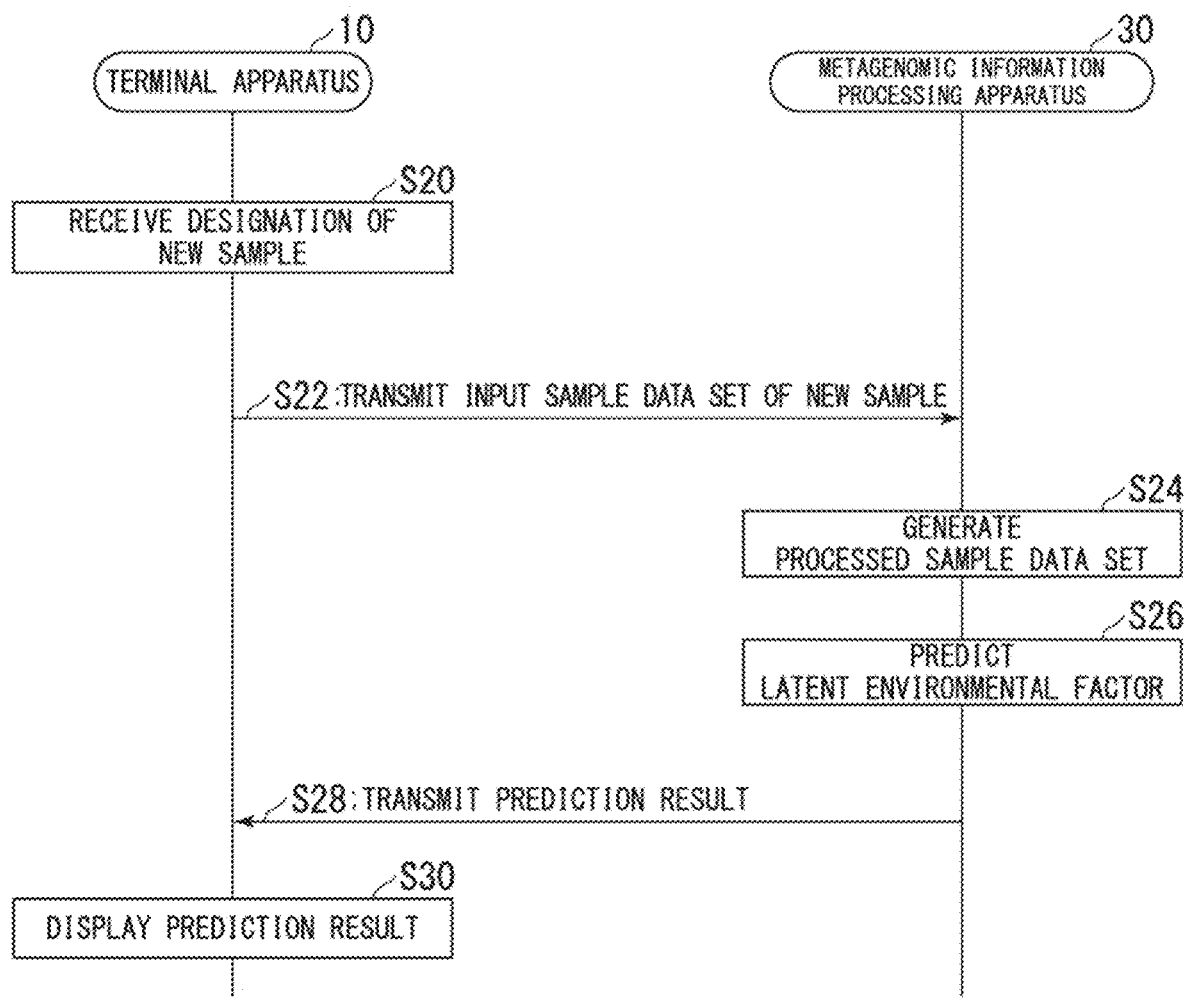
FIG. 10 is a sequence chart illustrating a flow of new sample prediction processing of the metagenomic information processing system according to the same embodiment.

FIG. 10 is a sequence chart illustrating a flow of new sample prediction processing of the metagenomic information processing system 1.

Figure 11:
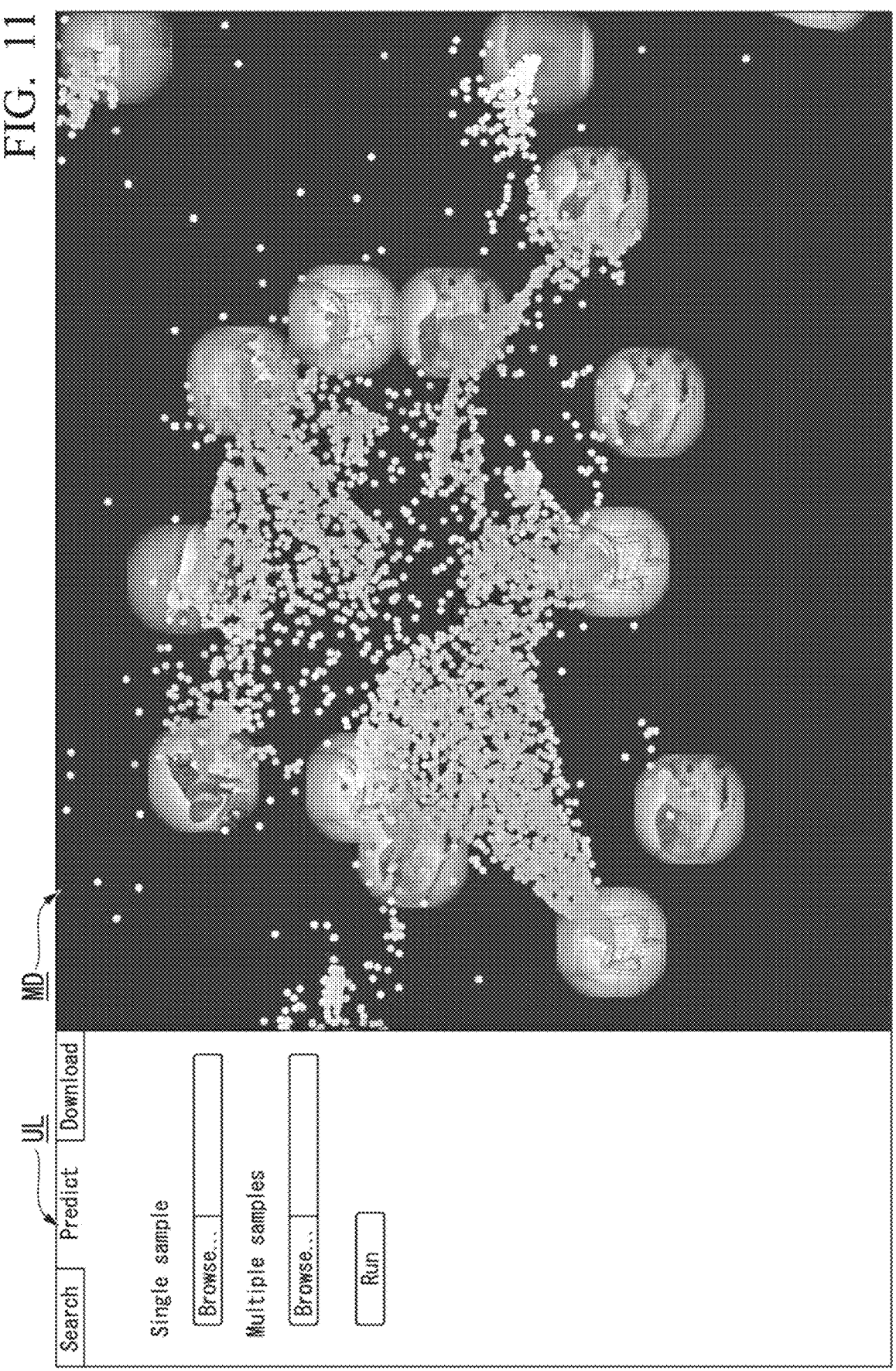
FIG. 11 is a view illustrating a third example of the display screen of the metagenomic information processing system according to the same embodiment.

(Step S20) The terminal apparatus 10 receives designation of a new sample (prediction target) from a user. For example, the terminal apparatus 10 may receive designation of a new sample in an upload file selection field UL illustrated in FIG. 11. Thereafter, the metagenomic information processing system 1 proceeds to Step S22 with the processing.

(Step S22) The terminal apparatus 10 transmits the input sample data pair of the new sample to the metagenomic information processing apparatus 30. Thereafter, the metagenomic information processing system 1 proceeds to Step S24 with the processing.

(Step S24) The metagenomic information processing apparatus 30 generates a processed sample data pair using the input sample data pair acquired from the terminal apparatus 10. Thereafter, the metagenomic information processing system 1 proceeds to Step S26 with the processing.

(Step S26) The metagenomic information processing apparatus 30 predicts a latent environmental factor of the new sample using the processed sample data pair generated in the processing of Step S24 and the metagenomic model. Thereafter, the metagenomic information processing system 1 proceeds to Step S28 with the processing.

(Step S28) The metagenomic information processing apparatus 30 transmits the prediction result to the terminal apparatus 10. Thereafter, the metagenomic information processing system 1 proceeds to Step S30 with the processing.

Figure 12:
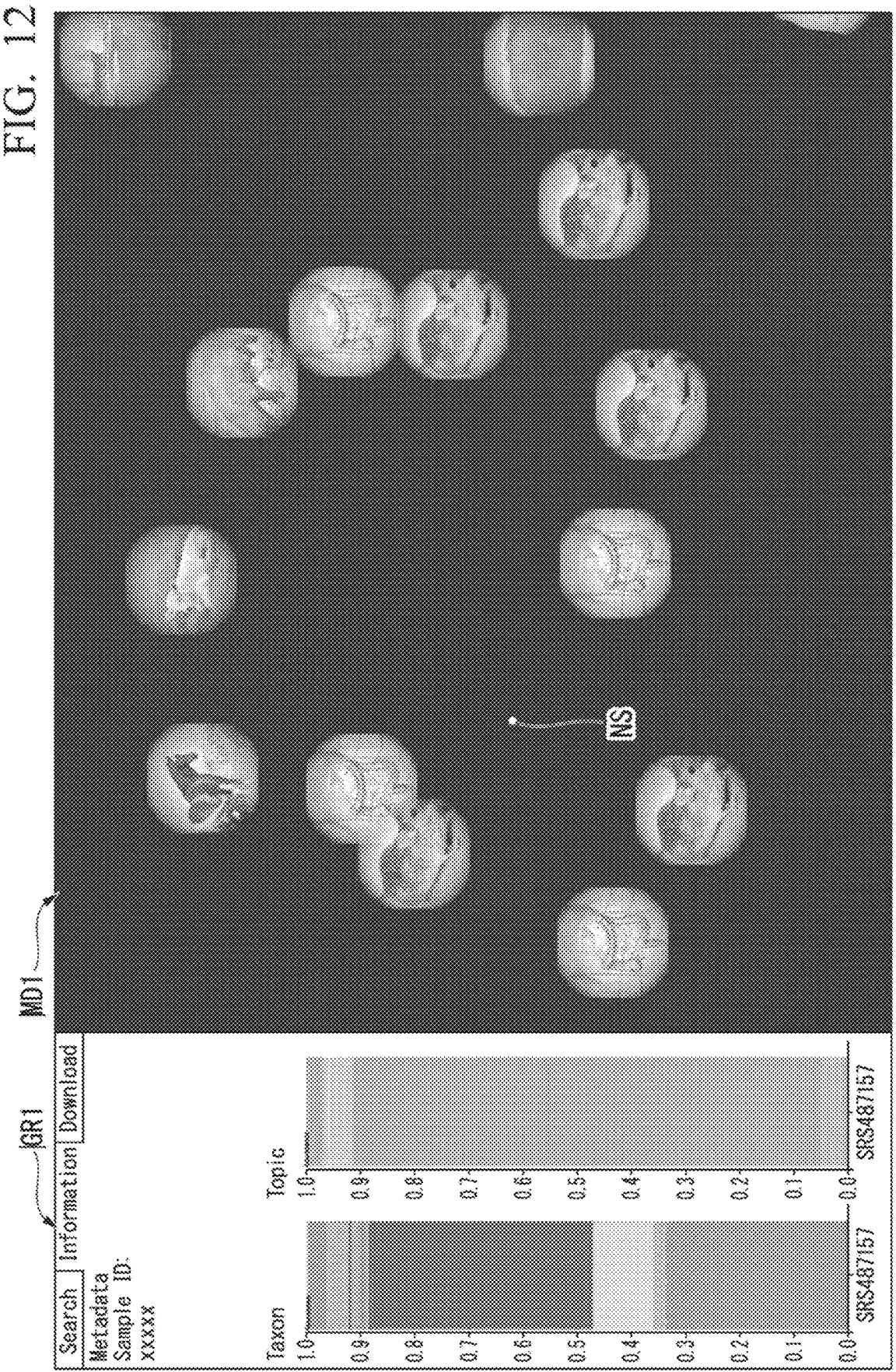
FIG. 12 is a view illustrating a fourth example of the display screen of the metagenomic information processing system according to the same embodiment.

(Step S30) The terminal apparatus 10 displays the prediction result acquired from the metagenomic information processing apparatus 30. For example, the terminal apparatus 10 may display the prediction result of the sample in a highlighted manner by displaying only a plot NS of the predicted sample as in a metagenomic model image MD1 of FIG. 12. In addition, the prediction result may be displayed by displaying the microbial community of the sample or the latent environmental factor constituting the sample in a bar graph GR1. Thereafter, the metagenomic information processing system 1 ends the processing illustrated in FIG. 10.

Next, an operation of the metagenomic information processing system 1 searching using a metagenomic model will be described.

Figure 13:
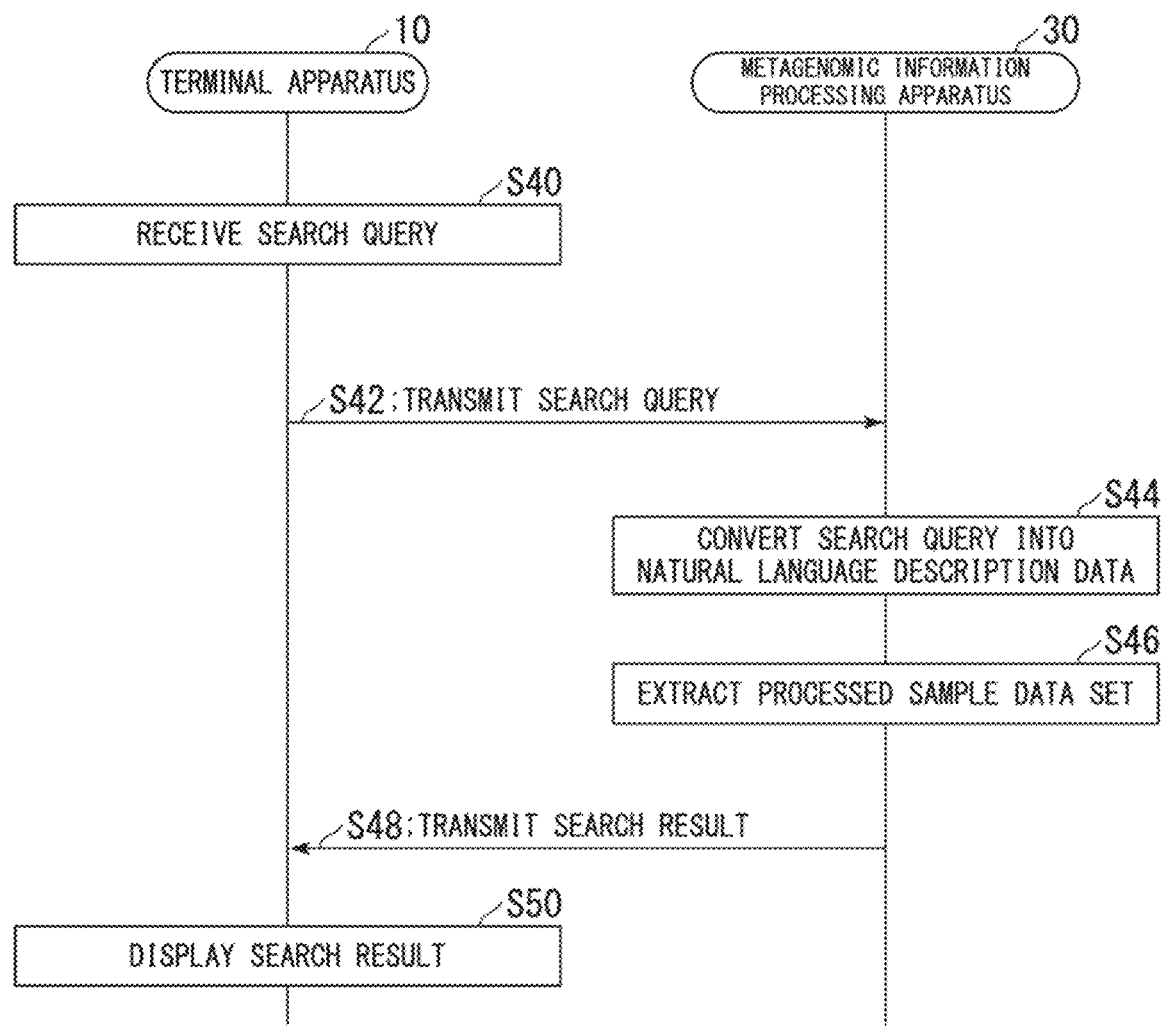
FIG. 13 is a sequence chart illustrating a flow of search processing of the metagenomic information processing system according to the same embodiment.

FIG. 13 is a sequence chart illustrating a flow of search processing of the metagenomic information processing system 1.

Figure 14:
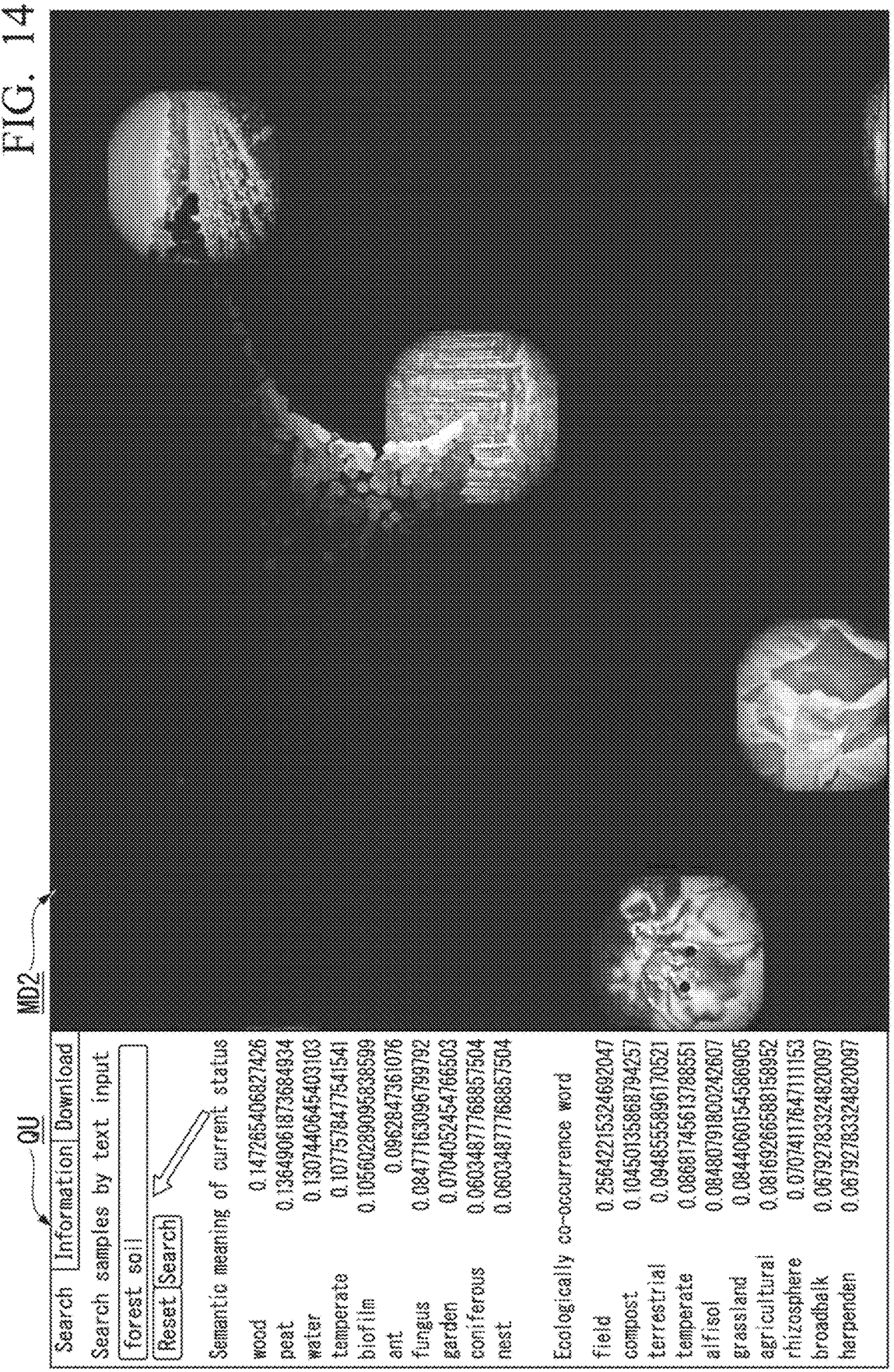
FIG. 14 is a view illustrating a fifth example of the display screen of the metagenomic information processing system according to the same embodiment.

(Step S40) The terminal apparatus 10 receives an input of a search query from a user. For example, the terminal apparatus 10 receives an input of a character string to a search query input field QU illustrated in FIG. 14 or designation of data describing the search query. Thereafter, the metagenomic information processing system 1 proceeds to Step S42 with the processing.

(Step S42) The terminal apparatus 10 transmits the search query to the metagenomic information processing apparatus 30. Thereafter, the metagenomic information processing system 1 proceeds to Step S44 with the processing.

(Step S44) The metagenomic information processing apparatus 30 converts the search query acquired from the terminal apparatus 10 into the natural language description data. Thereafter, the metagenomic information processing system 1 proceeds to Step S46 with the processing.

(Step S46) The metagenomic information processing apparatus 30 extracts the processed sample data pair using the natural language description data converted in Step S44 and the metagenomic model. For example, as illustrated in FIG. 15, the metagenomic information processing apparatus 30 calculates the score with respect to the search query for each processed sample data pair used for generating the metagenomic model and identifies the sample having a high score. Thereafter, the metagenomic information processing system 1 proceeds to Step S48 with the processing.

(Step S48) The metagenomic information processing apparatus 30 transmits the search result to the terminal apparatus 10. Thereafter, the metagenomic information processing system 1 proceeds to Step S50 with the processing.

(Step S50) The terminal apparatus 10 displays the search result acquired from the metagenomic information processing apparatus 30. For example, as in a metagenomic model image MD2 illustrated in FIG. 14, the terminal apparatus 10 displays the sample having a high correlationship with the search query in a highlighted manner by displaying plots of the samples at brightness corresponding to the score. Thereafter, the metagenomic information processing system 1 ends the processing illustrated in FIG. 13.

When the metagenomic model is utilized in searching in this manner, it is possible to flexibly search for a sample via the latent environmental factor, instead of perfect match searching having the natural language description data of the sample as a target. For example, when three words "hot spring water" are designated as a search query and samples of top ten scores are displayed (FIG. 15), the ten samples include many samples acquired from a hot-spring environment. On the other hand, a sample SRS005698 positioned at the top fifth of the score does not include any word of hot, spring, and water in its natural language description data. However, the SRS005698 includes a number of thermogymnomonas which are bacteria that inhabit hot springs. That is, in the metagenomic model, since the SRS005698 is predicted to be quite hot-spring-like environment, it is extracted by searching based on the search query of "hot spring water". In this manner, it is possible to acquire the sample expressing the search query in the viewpoint of the microbial community structure, by displaying the search result via the latent environmental factors instead of direct searching using searching words.

[Conclusion of Present Embodiment]

From the recent research, it has become clear that the microbial community structure data is not distributed in disorder in a space of all the parameters and has a pattern of a unique microbial presence amount in accordance with the environment (origin) where the sample is acquired. For example, it has been reported that a sample acquired from the river has a microbial community structure unique to fresh water, and a sample acquired from the ocean has a microbial community structure unique to sea water (Non-Patent Document 5). On the other hand, a case where the pattern of an environment recognized by humans does not necessarily match the pattern of the microbial community structure in some environments has also been reported. For example, in previous research related to the microbial community structure inside the human gut, it has been reported that entero-microbial community structures of three patterns irrelevant to the race and the gender are present, and a concept of enterotype has been advocated (Non-Patent Document 6). That is, it is not appropriate to collectively handle all the microbial community structures inside the human gut manifesting various patterns with only the single label of "inside human gut". That is, from the viewpoint of the microbial community structure, it is necessary to define the pattern of the environment with the granularity different from that recognized by humans.

Moreover, the problem goes beyond the granularity in the definition of the environmental pattern. Many natural environments are temporally and spatially continuous systems which cannot be segmented with discrete labels. For example, even in environments to which the same label "river" is applied, the microbial community structures present in a source basin, a basin of the river flowing in an urban area, and an estuary area are different from each other. Then, since these microbial community structures continuously change, it is not possible to perform strict segmentation.

As described above, the microbial community structure has the following features. Firstly, it may adopt various patterns which do not necessarily match the definition of the existing natural environments. Secondly, the patterns cannot be discretely clustered and may continuously change. In the future, in order to develop the technology using measurement of microbial community structures, such as diagnosis of health condition of humans, diagnosis of a natural environment, and a technology of controlling environments, it is necessary to employ a comparative analysis technique for microbial community structures in consideration of the features of the microbial community structure.

In this regard, the continuity of the microbial community structure data can be modeled by assuming that the microbial community in a sample consists of a mixture of several sub-communities. For example, a microbial community in a sample collected from an estuary area can be modeled in a state where a sub-community of a microbial community which inhabits fresh water and a sub-community of a microbial community which inhabits the ocean are mixed.

In this manner, on the assumption that the microbial community structure data is in a state where microbial communities originating in several environments are mixed, technologies of estimating the origin environment include SourceTracker (Non-Patent Document 1). The SourceTracker is software in which a user sets several pieces of microbial community structure data as source communities and a new sample is modeled as a mixture of the source communities.

It is possible to estimate the ratio at which the source communities are mixed to obtain a new sample as a result and to evaluate whether there is incorporation from another environment or contamination in the new sample by utilizing the SourceTracker. However, since the source communities set by a user are also the microbial community structure data, there is a possibility that they are also data in which several sub-communities are mixed. When the new sample and the source communities are data of a mixture, it is not appropriate to apply the assumption of the model described above, so that appropriate modeling cannot be performed. Therefore, when the pathway of incorporation or contamination is not clear, it is difficult to appropriately set the source communities which become the elements of the mixture.

In this regard, as described above, the metagenomic information processing system 1 (an example of an information processing system) according to the present embodiment includes the sample acquisition unit 341 (an example of a sample data acquisition unit) that acquires sample data (for example, a processed sample data pair) in which a microbial community including one or more microbes and a character string cluster including one or more character strings are associated with each other, and the model generation unit 344 (an example of a reference data acquisition unit) that acquires reference data (for example, latent environmental factors) in which a reference microbial community including at least a portion of microbes of the microbial community indicated by the sample data and a reference character string cluster including at least a portion of character strings of the character string cluster indicated by the sample data are associated with each other, based on a plurality of pieces of sample data. In the reference data acquired by the reference data acquisition unit, the microbial community indicated by the sample data includes the reference microbial community indicated by first reference data and the reference microbial community indicated by second reference data. The character string cluster indicated by the sample data includes the reference character string cluster indicated by the first reference data and the reference character string cluster indicated by the second reference data.

Accordingly, the metagenomic information processing system 1 identifies the latent environmental factor from the existing sample. That is, the metagenomic information processing system 1 can automatically perform work of identifying a latent environmental factor which is unlikely to be performed by manpower. In addition, since the latent environmental factor can be identified quantitatively and comprehensively by performing identification of the latent environmental factors through machine learning, it is possible to reduce a risk that the latent environmental factors become a combination of different factors or a risk that the latent environmental factors are neglected. Thus, the metagenomic information processing system 1 can facilitate interpretation or utilization of a microbial community.

In addition, the metagenomic information processing system 1 configures a function for appropriately projecting a sample in a two-dimensional space, based on the mixture ratio of the latent environmental factors.

Accordingly, the metagenomic information processing system 1 can easily confirm the relationship between samples.

In addition, the metagenomic information processing system 1 includes the sample prediction unit 345 (an example of an identification unit) that identifies the reference data configuring a set of the microbial community and the character string cluster indicated by the sample data (for example, a processed sample data pair of a new sample) which is not used for acquiring the reference data.

Accordingly, since the metagenomic information processing system 1 also identifies the latent environmental factors for a new sample, it is possible to dispose a new sample with another sample in a two-dimensional plane, for example. Thus, the metagenomic information processing system 1 can facilitate comparison between all the existing samples and the new sample.

In addition, in the metagenomic information processing system 1, the sample data includes the proportion of microbes in the microbial community and the proportion of character strings in the character string cluster, and the reference data includes the proportion of microbes in the reference microbial community and the proportion of character strings in the reference character string cluster.

Accordingly, the metagenomic information processing system 1 can exactly express the relationship between samples based on the mixture ratio of the latent environmental factors.

In addition, the metagenomic information processing system 1 includes the storage unit 32 (an example of a storage unit) that stores reference data (for example, latent environmental factors) in which the reference microbial community including one or more microbes and the reference character string cluster including one or more character strings are associated with each other, the model search request unit 154 (an example of an acquisition unit) that acquires a search query, and the model search unit 346 (an example of an extraction unit) that extracts reference data related to the search query.

Accordingly, the metagenomic information processing system 1 performs searching using a metagenomic model. Therefore, it is possible to perform searching by judging the similarity with respect to the search query in the characteristics of the microbial community, instead of simple coincidence of the character string with respect to the search query. Thus, the metagenomic information processing system 1 can facilitate interpretation or utilization of a microbial community.

MODIFICATION EXAMPLE

Hereinabove, an embodiment of this invention has been described in detail with reference to the drawings. However, the specific constitution is not limited to the foregoing embodiment and includes design and the like within a range not departing from the gist of this invention. For example, the constitutions described above in the foregoing embodiment can be arbitrarily combined. In addition, for example, each of the constitutions described above in the foregoing embodiment can be omitted when it is not necessary to exhibit a particular function.

The metagenomic information processing system 1 may present various pieces of information to a user, other than those described in the foregoing first embodiment. For example, the metagenomic information processing system 1 may present the degree of a difference between two samples. The metagenomic information processing system 1 may present the proportion of the individual latent environmental factors corresponding to the differential, regarding two samples including the same latent environmental factors. For example, when the microbial community of the latent environmental factors corresponding to the differential is added to the environment of one sample, it can approximate the environment of the other sample. Accordingly, an environment of a pathological (not desirable) microbial community can be an environment of a healthy (desirable) microbial community. In addition, for example, the metagenomic information processing system 1 may present the degree of a discrepancy from the latent environmental factors of a sample. For example, if the latent environmental factors are closely related to the disease state, the soundness may be able to be estimated from the degree of a discrepancy.

The metagenomic information processing system 1 may analyze not only samples acquired in different environments but also samples acquired in the same environments at different timings. A change in a microbial community in a certain environment can be traced by analyzing such time-series samples. In this case, the metagenomic information processing system 1 may present a warning in accordance with a change over time in the microbial community, for example, when it has changed into or is becoming an undesirable community.

In the first embodiment described above, a case where microbial community structure data is analyzed has been described, but the embodiment is not limited thereto. As described above, the metagenomic information processing system 1 is a system in which evaluation of the continuity of the sample or searching is executed by extracting a corresponding relationship as the latent environmental factors from natural number count data of two kinds (microbial community structure data and natural language description data) related to the same sample and visualizing the corresponding relationship based on the similarity of the latent environmental factors. In other words, it is possible to analyze biological data other than the microbial community structure data by preparing natural number count data of two kinds related to the same sample.

For example, the natural number count data may be generated using biological data such as base sequence data of small ribosomal subunit RNA including 16S ribosomal ribonucleic acid (rRNA), 18S rRNA, 23S rRNA, and the like used for phyletic analysis of the microbial community; metagenomic data (genetic component data); metatranscriptome data (gene expression amount data); and metabolome data (metabolic product data), as the analysis target. In this case, base sequence data or mass analysis data obtained by an experiment is converted into the natural number count data. That is, data quantitatively expressing the biomolecules is generated. The said biomolecules are molecules present inside the body of a living being or molecules composed by a living being. For example, the biomolecules include nucleic acid such as DNA and RNA, amino acid, peptide, protein, saccharinity, lipid, and hormone. In addition, the quantity indicates the presence amount (expression amount), activity, and the like. Hereinafter, the constitution of a case where biological data different from that in the first embodiment is analyzed will be described.

Modification Example 1: Metagenomic Data

First, a case where metagenomic data is used as an analysis target will be described. When metagenomic data is analyzed, microbial community structure data is replaced with metagenomic data.

FIG. 16 is a view illustrating a data structure of metagenomic data.

In the example illustrated in FIG. 16, the metagenomic data is configured to have sample IDs, pieces of gene name information, and pieces of quantitative information which are associated with each other. The gene name information indicates identification information of genetic products, that is, the names of genetic products, for example. The said genetic products include functional RNA and protein. The quantitative information is information indicating the quantities of the genetic products indicated by the gene name information. In this manner, the metagenomic data is data quantitatively expressing the features of the samples from the aspect of genetic products.

First, sets of contigs or scaffolds are constituted by executing a metagenomic sequence assembly with respect to a metagenomic shotgun lead obtained from an environmental sample. When an assembly is executed, it is possible to perform a de-novo assembly or the like using various sequence assembly tools specialized in metagenomic data. Next, a gene region is predicted from the constituted contigs or scaffolds using a gene prediction tool, and genetic sequences thereof are acquired.

Next, from the results of mapping of the metagenomic shotgun lead with respect to the contigs or the scaffolds, the lead coverage of the predicted genetic sequence is calculated, and the presence amount of each gene is estimated from the lead coverage information. At this time, since the probability of observation of a lead also increases in proportion to the length of the gene region, it is necessary to perform correction based on the length of the gene region when estimating the presence amount of the gene. Since the presence amount data is basically calculated as an actual value, the presence amount data is converted into integer value data through processing of rounding the actual value to the closest integer value.

Lastly, in order to estimate the function of the predicted gene region, sequence similarity searching is executed with respect to various amino acid sequence databases. The function is assigned to each gene region based on the sequence similarity.

Through the foregoing processing, metagenomic data can be acquired as the natural number count data indicating genetic products and the presence amounts of the genetic products. Similar to the first embodiment, the natural language description data can be acquired by processing the data describing details and the like of each sample with a natural language. Then, processing similar to that in the first embodiment is performed using the metagenomic data and the natural language description data, and a probability model expressing each sample as a linear combination of a plurality of latent factors is generated. Consequently, the corresponding relationship between the reference cluster of the genetic products and the reference cluster of the character strings can be extracted.

Modification Example 2: Metatranscriptomic Data

Next, a case where metatranscriptome data is used as an analysis target will be described. When metatranscriptome data is analyzed, microbial community structure data is replaced with metatranscriptome data. Since the data configuration of metatranscriptome data is similar to that of metagenomic data, description will be omitted. However, the case of metatranscriptome data differs from the foregoing case in that the genetic product is mainly messenger RNA (mRNA).

Generation of metatranscriptome data will be described. In the case of metatranscriptome, in order to reduce the influence of a large amount of rRNA present in the sample, it is necessary to appropriately eliminate rRNA during sample refinement performed before sequencing or during information processing performed after sequencing.

Next, the obtained lead is mapped with the existing microbial genomic sequence. Alternatively, similar to the case of the metagenomic data, gene prediction is performed by forming contigs using an assembly, and the gene expression amount is estimated from the lead mapping result and the correction calculation performed based on the length of the gene. Moreover, sequence similarity searching is performed for the predicted gene using the base sequence database, thereby estimating the function.

Through the foregoing processing, metatranscriptome data can be acquired as the natural number count data indicating mRNA and the expression amounts of the mRNA. Similar to the first embodiment, the natural language description data can be acquired by processing the data describing details and the like of each sample with a natural language. Then, processing similar to that in the first embodiment is performed using the metatranscriptome data and the natural language description data, and a probability model expressing each sample as a linear combination of a plurality of latent factors is generated. Consequently, the corresponding relationship between the reference cluster of the mRNA and the reference cluster of the character strings can be extracted.

Modification Example 3: Metabolomic Data

Next, a case where metabolome data is used as an analysis target will be described. When metabolome data is analyzed, microbial community structure data is replaced with metabolome data.

FIG. 17 is a view illustrating a data structure of metabolome data.

In the example illustrated in FIG. 17, metabolome data is configured to have sample IDs, pieces of molecule name information, and pieces of quantitative information which are associated with each other. The molecule name information indicates identification information of molecules of metabolic products and the like, that is, the name of molecules, for example. The quantitative information is information indicating the quantities of the molecules indicated by the molecule name information. In this manner, metabolome data is data quantitatively expressing the features of the samples from the aspect of molecules.

Next, generation of metabolome data will be described. For generation of metabolome data, it is possible to utilize a comprehensive measurement result of small molecules of a metabolic product (an intermediate or an end product of a plurality of enzyme reactions) and the like in an environmental sample acquired by a technology such as a nuclear magnetic resonance method, a gas chromatography mass analysis method, a liquid chromatography mass analysis method, and a capillary electrophoresis mass analysis method.

In the case of the nuclear magnetic resonance method, a chemical shift is analyzed, and in the case of the mass analysis method, the pattern of spectrum data of a mass-to-charge ratio is analyzed. Identification of the kind and estimation of the quantity of metabolic products in the sample are performed. Processing such as filtering of nose based on a frequency filter, a threshold, or the like, peak detection, separation based on chromatography or the like may be performed with respect to the spectrum data. In addition, in the case of the mass analysis method, processing such as alignment of spectrums, normalization of a peak intensity between samples, and decomposition of overlapping of the peaks of different metabolic products may be performed.

Next, the metabolic product of each peak is identified using a reference spectrum database, the quantity of each metabolic product is estimated from intensity information of the spectrum peak. Through the foregoing processing, metabolome data can be acquired as the natural number count data indicating the metabolic product (molecules) and the density of each metabolic product. Similar to the first embodiment, the natural language description data can be acquired by processing the data describing details and the like of each sample with a natural language. Then, processing similar to that in the first embodiment is performed using the metabolome data and the natural language description data, and a probability model expressing each sample as a linear combination of a plurality of latent factors is generated. Consequently, the corresponding relationship between the reference cluster of the metabolic products and the reference cluster of the character strings can be extracted.

As described above, analysis may be performed while having the metagenomic data, the metatranscriptome data, and the metabolome data associated with the natural language description data of the sample. Since all of the pieces of data eventually become the natural number count data, another piece of the natural number count data from which the corresponding relationship is extracted is not necessarily the natural language description data of the sample. Specifically, it is possible to apply the data to an arbitrary combination of the microbial community structure data, the metagenomic data, the metatranscriptome data, the metabolome data, the natural language description data, and the like. For example, when the microbial community structure data and the metabolome data are analyzed as a pair, the extracted corresponding relationship forms a pair of a reference microbial cluster and a reference metabolic product cluster which co-occur between the samples.

That is, the metagenomic information processing system 1 described above can be expanded in accordance with data of an analysis target. For example, this information processing system includes the sample data acquisition unit that acquires sample data in which a first element cluster including one or more first biological elements (for example, the names of living beings, genetic products, and biomolecules of metabolic products and the like) and a second element cluster including one or more second biological elements (for example, elements of the names of living beings, genetic products, and biomolecules of metabolic products and the like different from the first biological elements) are associated with each other; and the reference data acquisition unit that acquires reference data in which a first reference element cluster including at least a portion of the first biological elements of the first element cluster indicated by the sample data and a second reference element cluster including at least a portion of the second biological elements of the second element cluster indicated by the sample data are associated with each other, based on a plurality of pieces of the sample data. The first element cluster indicated by the sample data includes the first reference element cluster indicated by the first reference data and the first reference element cluster indicated by the second reference data of the plurality of pieces of the reference data acquired by the reference data acquisition unit. The second element cluster indicated by the sample data includes the second reference element cluster indicated by the first reference data and the second reference element cluster indicated by the second reference data.

Similarly, for example, this information processing system includes the storage unit that stores the reference data in which the first reference element cluster and the second reference element cluster are associated with each other, the acquisition unit that acquires a search query indicating at least any of the first biological element and the second biological element, and the extraction unit that extracts the reference data related to the search query.

In place of the second biological elements, character strings may be applied, as described above.

According to an aspect of the present embodiment, there is provided an information processing system including a sample data acquisition unit that acquires, for each sample, sample data in which a first cluster including a plurality of sets of a biological element detected from the sample and a biological element quantity indicating a quantity of the biological element and a second cluster including a plurality of sets of a morpheme regarding text describing an environment in which the sample is present and an appearance frequency of the morpheme are associated with each other; and a generation unit that analyzes a plurality of pieces of the sample data with the biological element quantity and the appearance frequency as parameters and generates information indicating a relationship between the environment and the first cluster.

According to the aspect of the present embodiment, in the information processing system, the generation unit acquires a plurality of pieces of reference data in which a reference biological element cluster including a plurality of sets of information indicating at least a portion of the biological elements and the quantity of the biological element and a reference morpheme cluster including a plurality of sets of at least a portion of the morphemes and the appearance frequency of the morpheme are associated with each other, based on analysis of the plurality of pieces of the sample data. The first cluster indicated by the sample data includes a reference biological element cluster indicated by first reference data and a reference biological element cluster indicated by second reference data of the plurality of pieces of the reference data, and the second cluster indicated by the sample data includes a reference morpheme cluster indicated by the first reference data and a reference morpheme cluster indicated by the second reference data.

According to the aspect of the present embodiment, in the information processing system, the generation unit estimates a topic using topic modeling and acquires the topic as the reference data.

According to the aspect of the present embodiment, the information processing system further includes a storage unit that stores the reference data, an acquisition unit that acquires a search query indicating at least any of the biological element and the morpheme, and an extraction unit that extracts the reference data related to the search query.

According to the aspect of the present embodiment, in the information processing system, the biological element is a microbe.

According to the aspect of the present embodiment, in the information processing system, the biological element is a biomolecule.

According to another aspect of the present embodiment, there is provided an information processing method in an information processing system, including a first step of acquiring, for each sample, sample data in which a first cluster including a plurality of sets of a biological element detected from the sample and a biological element quantity indicating a quantity of the biological element and a second cluster including a plurality of sets of a morpheme regarding text describing an environment in which the sample is present and an appearance frequency of the morpheme are associated with each other; and a second step of analyzing a plurality of pieces of the sample data with the biological element quantity and the appearance frequency as parameters and generating information indicating a relationship between the environment and the first cluster.

According to another aspect of the present embodiment, there is provided a program in a computer, including a first step of acquiring, for each sample, sample data in which a first cluster including a plurality of sets of a biological element detected from the sample and a biological element quantity indicating a quantity of the biological element and a second cluster including a plurality of sets of a morpheme regarding text describing an environment in which the sample is present and an appearance frequency of the morpheme are associated with each other; and a second step of analyzing a plurality of pieces of the sample data with the biological element quantity and the appearance frequency as parameters and generating information indicating a relationship between the environment and the first cluster.

According to another aspect of the present embodiment, there is provided an information processing apparatus including a sample data acquisition unit that acquires, for each sample, sample data in which a first cluster including a plurality of sets of a biological element detected from the sample and a biological element quantity indicating a quantity of the biological element and a second cluster including a plurality of sets of a morpheme regarding text describing an environment in which the sample is present and an appearance frequency of the morpheme are associated with each other; and a generation unit that analyzes a plurality of pieces of the sample data with the biological element quantity and the appearance frequency as parameters and generates information indicating a relationship between the environment and the first cluster.

In addition, processing as the terminal apparatus 10, the metagenomic information processing apparatus 30, and the sample accumulation apparatus 50 may be performed by recording a program for realizing the functions of the terminal apparatus 10, the metagenomic information processing apparatus 30, and the sample accumulation apparatus 50 described above in a computer readable record medium, and causing a computer system to read and execute the program recorded in this record medium. Here, the expression "causing a computer system to read and execute the program recorded in the record medium" includes installation of the program in the computer system. The said "computer system" includes hardware such as an OS and peripherals. In addition, "the computer system" may include a plurality of computer apparatuses connected via a network including a communication line such as the internet, a WAN, a LAN, and a dedicated line. In addition, "the computer readable record medium" indicates a storage device such as a portable medium including a flexible disk, a magneto-optical disk, a ROM, and a CD-ROM, and a hard disk built in the computer system. In this manner, the record medium in which the program is stored may be a non-temporary record medium such as a CD-ROM. In addition, the record medium includes a record medium which is provided inside or outside and can be accessed through a distribution server to distribute the program. The code of the program stored in the record medium of the distribution server may be different from the code of a program of the type which can be executed by the terminal apparatus. That is, the type of storage in the distribution server does not matter as long as it is installed in a form in which it can be downloaded from the distribution server and executed by the terminal apparatus. A configuration in which the program is divided into a plurality of programs and they are united in the terminal apparatus after being downloaded at timings different from each other may be adopted, and the distribution servers distributing each of the divided programs may be different from each other. Moreover, "the computer readable record medium" includes a medium which retains the program for a certain period of time, such as a server in a case where the program is transmitted via a network or a volatile memory (RAM) inside a computer system which becomes a client. In addition, the program may be a program for realizing a portion of the functions described above. Moreover, the program may be a program which can be realized by combining the functions described above with a program that is already recorded in the computer system, that is, a so-called differential file (differential program).

In addition, a part or all of the functions of the terminal apparatus 10, the metagenomic information processing apparatus 30, and the sample accumulation apparatus 50 described above may be realized as an integrated circuit such as large scale integration (LSI). Each of the functions described above may individually serve as a processor or may serve as a processor in which a portion or the entirety is integrated. In addition, the technique for an integrated circuit is not limited to the LSI and may be realized through a dedicated line or a general purpose processor. In addition, when an integrated circuit technology comes out to replace the LSI as a result of advance of the semiconductor technology, an integrated circuit according to such a technology may be used.

INDUSTRIAL APPLICABILITY

An aspect of the present invention can be utilized in computers, servers, portable terminals (tablets and smartphones), integrated circuits, and programs, for example.

DESCRIPTION OF REFERENCE SYMBOLS

1 Metagenomic information processing system
10 Terminal apparatus
11 Communication unit
12 Input unit
13 Display unit
14 Storage unit
141 Input sample storage unit
15 Control unit
151 Input sample contribution unit
152 Model presentation unit
153 Sample prediction request unit
154 Model search request unit
30 Metagenomic information processing apparatus
31 Communication unit
32 Storage unit
331 Processed sample storage unit
332 Model storage unit
34 Control unit
341 Sample acquisition unit
342 Text processing unit
343 Phyletic component processing unit
344 Model generation unit
345 Sample prediction unit
346 Model search unit
50 Sample accumulation apparatus

The invention claimed is:
1. An information processing system comprising:
a sample data acquisition unit that acquires, for each sample, sample data in which a first cluster and a second cluster are associated with each other, the first cluster including a plurality of sets of a biological element detected from the sample and a biological element quantity indicating a quantity of the biological element, the second cluster including a plurality of sets of a morpheme regarding text describing an environment in which the sample is present and an appearance frequency of the morpheme; and
a generation unit that analyzes a plurality of pieces of the sample data with the biological element quantity and the appearance frequency as parameters and generates information indicating a relationship between the environment and the first cluster.
2. The information processing system according to claim 1,
wherein the generation unit acquires a plurality of pieces of reference data in which a reference biological element cluster and a reference morpheme cluster are associated with each other, the reference biological element cluster including a plurality of sets of information indicating at least a portion of the biological elements and the quantity of the biological element, the reference morpheme cluster including a plurality of sets of at least a portion of the morphemes and the appear- ance frequency of the morpheme, the acquisition being performed based on analysis of the plurality of pieces of the sample data, and wherein the first cluster indicated by the sample data includes a reference biological element cluster indicated by first reference data and a reference biological element cluster indicated by second reference data of the plurality of pieces of the reference data, and the second cluster indicated by the sample data includes a reference morpheme cluster indicated by the first reference data and a reference morpheme cluster indicated by the second reference data.

3. The information processing system according to claim 2, wherein the generation unit estimates a topic using topic modeling and acquires the topic as the reference data.

4. The information processing system according to claim 2, the information processing system further comprising:

a storage unit that stores the reference data;

an acquisition unit that acquires a search query indicating at least any of the biological element and the morpheme; and an extraction unit that extracts the reference data related to the search query.

5. The information processing system according claim 1, wherein the biological element is a microbe.

6. The information processing system according to claim 1, wherein the biological element is a biomolecule.

7. An information processing method in an information processing system, the information processing method comprising:

acquiring, for each sample, sample data in which a first cluster and a second cluster are associated with each other, the first cluster including a plurality of sets of a biological element detected from the sample and a biological element quantity indicating a quantity of the biological element, the second cluster including a plurality of sets of a morpheme regarding text describing an environment in which the sample is present and an appearance frequency of the morpheme; and analyzing a plurality of pieces of the sample data with the biological element quantity and the appearance frequency as parameters and generating information indicating a relationship between the environment and the first cluster.

8. A non-transitory computer readable recording medium storing a program in a computer, the program comprising:

acquiring, for each sample, sample data in which a first cluster and a second cluster are associated with each other, the first cluster including a plurality of sets of a biological element detected from the sample and a biological element quantity indicating a quantity of the biological element, the second cluster including a plurality of sets of a morpheme regarding text describing an environment in which the sample is present and an appearance frequency of the morpheme; and analyzing a plurality of pieces of the sample data with the biological element quantity and the appearance frequency as parameters and generating information indicating a relationship between the environment and the first cluster.

9. An information processing apparatus comprising:

a sample data acquisition unit that acquires, for each sample, sample data in which a first cluster and a second cluster are associated with each other, the first cluster including a plurality of sets of a biological element detected from the sample and a biological element quantity indicating a quantity of the biological element, the second cluster including a plurality of sets of a morpheme regarding text describing an environment in which the sample is present and an appearance frequency of the morpheme; and a generation unit that analyzes a plurality of pieces of the sample data with the biological element quantity and the appearance frequency as parameters and generates information indicating a relationship between the environment and the first cluster.

* * * * *